(12) United States Patent
Schottek et al.

(10) Patent No.: US 7,157,398 B2
(45) Date of Patent: Jan. 2, 2007

(54) COVALENTLY FIXED NONMETALLOCENES, PROCESS FOR PREPARING THEM AND THEIR USE FOR THE POLYMERIZATION OF OLEFINS

(75) Inventors: Jörg Schottek, Frankfurt (DE); Jörg Schulte, Frankfurt (DE); Tim Dickner, Frankfurt (DE); Iris Küllmer, Frankfurt (DE)

(73) Assignee: Celanese Ventures GmbH (DE)

( * ) Notice: Subject to any disclaimer, the term of this patent is extended or adjusted under 35 U.S.C. 154(b) by 155 days.

(21) Appl. No.: 10/505,684

(22) PCT Filed: Feb. 26, 2003

(86) PCT No.: PCT/EP03/01934

§ 371 (c)(1),
(2), (4) Date: Jan. 21, 2005

(87) PCT Pub. No.: WO03/072584

PCT Pub. Date: Sep. 4, 2003

(65) Prior Publication Data

US 2005/0148461 A1 Jul. 7, 2005

(30) Foreign Application Priority Data

Feb. 26, 2002 (DE) ................. 102 08 252

(51) Int. Cl.
*B01J 31/00* (2006.01)
*B01J 37/00* (2006.01)
*C08F 4/02* (2006.01)
*C08F 4/60* (2006.01)

(52) U.S. Cl. .............. 502/102; 502/103; 502/154; 502/155; 502/159; 526/160; 526/161; 526/172

(58) Field of Classification Search ................ 502/102, 502/103, 154, 155, 159; 526/160, 161, 172
See application file for complete search history.

(56) References Cited

U.S. PATENT DOCUMENTS

| | | | |
|---|---|---|---|
| 6,124,231 A | 9/2000 | Fritze et al. | |
| 6,255,531 B1 | 7/2001 | Fritz et al. | |
| 6,271,164 B1 | 8/2001 | Fritze et al. | |
| 6,329,313 B1 | 12/2001 | Fritze et al. | |
| 6,344,492 B1 * | 2/2002 | Borovik et al. | ............ 521/31 |
| 6,350,829 B1 | 2/2002 | Lynch et al. | |
| 6,380,276 B1 * | 4/2002 | Borovik et al. | ............ 521/153 |
| 6,589,948 B1 * | 7/2003 | Malfroy-Camine et al. | .. 514/185 |
| 6,709,824 B1 * | 3/2004 | Jacobsen et al. | ............ 435/6 |
| 6,720,434 B1 * | 4/2004 | Kim et al. | ............ 549/523 |
| 6,756,195 B1 * | 6/2004 | Weinberg et al. | ............ 435/4 |
| 6,841,667 B1 * | 1/2005 | Jacobsen et al. | ............ 540/604 |
| 6,884,749 B1 * | 4/2005 | Neal-Hawkins et al. | .... 502/120 |

FOREIGN PATENT DOCUMENTS

| | | |
|---|---|---|
| DE | 196 06 167 | 8/1997 |
| DE | 196 22 207 | 12/1997 |
| EP | 0 302 424 | 2/1989 |
| EP | 0 601 830 | 6/1994 |
| EP | 0 811 627 | 12/1997 |
| EP | 0 824 112 | 2/1998 |
| EP | 0 824 113 | 2/1998 |
| EP | 0 874 005 | 10/1998 |
| EP | 0 924 223 | 6/1999 |
| EP | 1 013 674 | 6/2000 |
| WO | WO-94/28034 | 12/1994 |
| WO | WO-97/11775 | 4/1997 |
| WO | WO-99/40129 | 8/1999 |
| WO | WO 0056786 A * | 9/2000 |
| WO | WO 03084662 A2 * | 10/2003 |

OTHER PUBLICATIONS

Phan, et al., "A facile method for catalyst immobilisation on silica: nickel-catalysed Kumada reactions in mini-continuous flow and batch reactors", Green Chem., 2004 (6) 526-532.*

Annis, et al., "Polymer-Supported Chiral Co(salen) Complexes: Synthetic Applications and Mechanistic Investigations in the Hydrolytic Kinetic Resolution of Terminal Expoxides", J. Am. Chem. Soc., 1999 (121) 4147-4154.*

* cited by examiner

Primary Examiner—J. A. Lorengo
Assistant Examiner—Jennine Brown
(74) Attorney, Agent, or Firm—Connolly Bove Lodge & Hutz

(57) ABSTRACT

The invention relates to a method for producing special transition metal compounds, to novel transition metal compounds and to the use thereof for polymerizing olefins.

20 Claims, No Drawings

COVALENTLY FIXED NONMETALLOCENES, PROCESS FOR PREPARING THEM AND THEIR USE FOR THE POLYMERIZATION OF OLEFINS

The present invention relates to a process for preparing specific transition metal compounds, novel transition metal compounds and their use for the polymerization of olefins.

In recent years, olefin polymerization has been carried out using not only conventional Ziegler catalysts but also metallocenes to generate polyolefins having particular properties which are not achieved using conventional Ziegler catalysts. Metallocenes can, if appropriate in combination with one or more cocatalysts, be used as catalyst components for the polymerization and copolymerization of olefins. In particular, halogen-containing metallocenes are used as catalyst precursors which can be converted, for example by means of an aluminoxane, into a polymerization-active cationic metallocene complex.

However, the preparation and use of metallocenes is still a cost factor which has not been able to be overcome either by means of increased activity or by means of improved synthetic methods. In addition, making such catalysts heterogeneous presents a further problem, since this greatly decreases the activities compared to the polymerization carried out by homogeneous catalysis.

Various "nonmetallocenes" which give advantages in terms of their preparation and costs of the starting materials are described in the literature, e.g. in EP 874 005. The high activities of these complexes represent a further cost-saving factor.

Some of these compounds are supported in order to improve the morphology of the polymer. However, since these compounds are merely physisorbed on the support material, detachment of the catalyst system (bleeding) occurs during the polymerization. This phenomenon is undesirable and leads to polymers having poor morphologies.

It is therefore an object of the invention to develop novel metal catalysts which make a new advantageous route to polyolefins possible while avoiding the disadvantages of the prior art described.

It has now surprisingly been found that a covalently bound novel ligand structure can be built up from substituted or unsubstituted amino phases (amine functions which are bound to silica via a spacer) and substituted or unsubstituted salicylaldehydes and can subsequently be reacted with metal compounds to give novel covalently bound metal complexes. This method of preparation represents a universal route to this novel class of compounds. These compounds thus achieve the object of the invention.

The invention provides compounds of the formula (I)

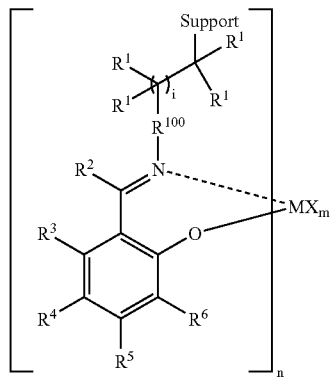

where $M^1$ is a metal of transition group III, IV, V or VI of the Periodic Table of the Elements, in particular Ti, Zr, Hf, Ni, Co, Fe, Pd, Sc, Cr and Nb, $R^1$, $R^2$, $R^3$, $R^4$, $R^5$, $R^6$ are identical or different and are each a hydrogen atom, a halogen atom or $Si(R^{10})_3$, where the radicals $R^{10}$ are identical or different and are each a hydrogen atom or a $C_1$–$C_{40}$ group, or $R^1$, $R^2$, $R^3$, $R^4$, $R^5$, $R^6$ are identical or different and are each a $C_1$–$C_{30}$ group, or two or more radicals $R^1$ and/or two or more radicals $R^2$ to $R^6$ can be joined to one another in such a way that the radicals $R^1$ or $R^2$ to $R^6$ and $R^{10}$ and the atoms connecting them form a $C_4$–$C_{24}$ ring system which may in turn be substituted, and the radicals $R^{100}$ are identical or different and can each be a $C_1$–$C_{40}$ group, and n is an integer from 1 to 4, preferably 2, and m is an integer from 0 to 4, preferably 2, and i is an integer from 1 to 100, preferably from 1 to 50, and the radicals X can be identical or different and are each a hydrogen atom, a $C_1$–$C_{10}$-hydrocarbon group such as $C_1$–$C_{10}$-alkyl or $C_6$–$C_{10}$-aryl, a halogen atom or $OR^9$, $SR^9$, $OSiR_3^9$, $SiR_3^9$, $PR_2^9$ or $NR_2^9$, where $R^9$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or the radicals L are each a toluenesulphonyl, trifluoroacetyl, trifluoracetoxyl, trifluoromethanesulphonyl, nonafluorobutanesulphonyl or 2,2,2-trifluoromethanesulphonyl group.

For the purposes of the present invention, a $C_1$–$C_{40}$ group is preferably $C_1$–$C_{40}$-alkyl, in particular $C_1$–$C_{20}$-alkyl, particularly preferably methyl, ethyl, n- or i-propyl, tert-butyl, n-pentyl, n-hexyl, cyclohexyl or octyl, $C_1$–$C_{10}$-fluoroalkyl, $C_1$–$C_{12}$-alkoxy, $C_6$–$C_{20}$-aryl, in particular phenyl and biphenyl, $C_6$–$C_{10}$-fluoroaryl, in particular tetrafluorophenyl, $C_6$–$C_{10}$-aryloxy, $C_2$–$C_{10}$-alkenyl, $C_7$–$C_{40}$-arylalkyl, $C_7$–$C_{40}$-alkylaryl, $C_5$–$C_{24}$-heteroaryl or $C_8$–$C_{40}$-arylalkenyl.

For the purposes of the present invention, the term $C_1$–$C_{30}$ group preferably refers to $C_1$–$C_{30}$-alkyl, in particular methyl, ethyl, n- or i-propyl, tert-butyl, n-pentyl, n-hexyl, cyclohexyl or octyl, $C_2$–$C_{25}$-alkenyl, $C_3$–$C_{15}$-alkylalkenyl, $C_6$–$C_{24}$-aryl, in particular phenyl and biphenyl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, in particular tetrafluorophenyl, fluorinated $C_7$–$C_{30}$-arylalkyl, fluorinated $C_7$–$C_{30}$-alkylaryl or $C_1$–$C_{10}$-alkoxy.

Particular preference is given to compounds of the formula (I) in which $M^1$ is Ti, Zr or Hf, particularly preferably zirconium, and $R^1$, $R^2$, $R^3$, $R^4$, $R^5$, $R^6$ are identical or different and are each a hydrogen atom, a halogen atom or $Si(R^{10})_3$, where the radicals $R^{10}$ are identical or different and are each a hydrogen atom or a $C_1$–$C_{40}$ group as defined above or $R^1$, $R^2$, $R^3$, $R^4$, $R^5$, $R^6$ are identical or different and are each a $C_1$–$C_{30}$ group as defined above, or two or more radicals $R^1$ and/or two or more radicals $R^2$ to $R^6$ can be joined to one another in such a way that the radicals $R^1$ or $R^2$ to $R^6$ and $R^{10}$ and the atoms connecting them form a $C_4$–$C_{24}$ ring system which may in turn be substituted, and the radicals $R^{100}$ are identical or different and are each a $C_1$–$C_{40}$ group, and n is an integer from 1 to 4, preferably 2, and m is an integer from 0 to 4, preferably 2, and i is an integer from 1 to 100, preferably 2, and X is a halogen atom, in particular chlorine, or a $C_1$–$C_{18}$ alkyl group, particularly preferably methyl, ethyl, n- or i-propyl, tert-butyl, n-pentyl, n-hexyl, cyclohexyl or octyl, or a $C_6$–$C_{15}$-aryl group, or substituted or unsubstituted phenoxides.

Very particular preference is given to compounds of the formula (I) in which $M^1$ is zirconium, $R^1$, $R^2$, $R^3$, $R^4$, $R^5$, $R^6$ are each a hydrogen atom or a linear or branched $C_1$–$C_{12}$-alkyl group, preferably methyl, ethyl, n-butyl, n-hexyl, isopropyl, isobutyl, isopentyl, cyclohexyl, cyclopentyl or octyl, particularly preferably methyl, ethyl, isopropyl or cyclohexyl, or a halogen atom or $C_5$–$C_{18}$-heteroaryl, or $C_7$–$C_{12}$-arylalkyl, or $C_7$–$C_{12}$-alkylaryl, or fluorinated $C_1$–$C_8$-alkyl, or fluorinated $C_6$–$C_{18}$-aryl, or fluorinated $C_7$–$C_{12}$-arylalkyl or fluorinated $C_7$–$C_{12}$-alkylaryl, and the radicals $R^{100}$ are identical or different and are each $C_1$–$C_{20}$-alkyl, in particular methylene, ethylene, $C_1$–$C_{10}$-fluoroalkyl, $C_1$–$C_{10}$-alkoxy, $C_6$–$C_{20}$-aryl, in particular phenyl, biphenyl, $C_6$–$C_{10}$-fluoroaryl, in particular 1,2,4,5-tetrafluorophenyl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, fluorinated $C_1$–$C_{25}$-alkyl, and n is 2, and m is 2, and i is 3, 4, 5, 6, 7, 8, 9 or 10, and X is a halogen atom, in particular chlorine, or a $C_1$–$C_{18}$-alkyl group, in particular methyl, ethyl, n-butyl, n-hexyl, isopropyl, isobutyl, isopentyl, cyclohexyl, cyclopentyl or octyl, or a $C_6$–$C_{15}$-aryl group, or substituted or unsubstituted phenoxides.

The invention further provides covalently supported metal compounds of the formula (II) in which the radicals are as defined under the formula (I).

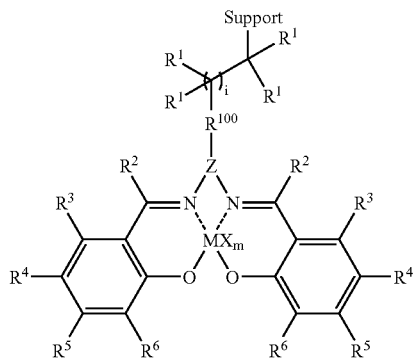

(II)

where

Z is a bridging structural element having the formula $M^5R^{13}R^{14}$, where $M^5$ is silicon or carbon and $R^{13}$ and $R^{14}$ are identical or different and are each a $C_1$–$C_{40}$ group or trimethylsilyl, or Z is boron, sulphur, phosphorus or nitrogen.

Z is preferably $CH_2$, $CH_2CH_2$, $CH(CH_3)CH_2$, $CH(C_4H_9)$ $C(CH_3)_2$, $C(CH_3)_2$, $(CH_3)_2Si$, $(CH_3)_3Si$—$Si(CH_3)$, boron, phosphorus.

Supports for the amino functions are inorganic polymers, organic polymers or organic copolymers, and particularly preferred supports are silica, polystyrene, polystyrene-divinylbenzene copolymer and polyethylene glycol materials which form the radical $R^{200}$. The amino groups can, as depicted in the following diagram, be attached to the polymer via various spacers.

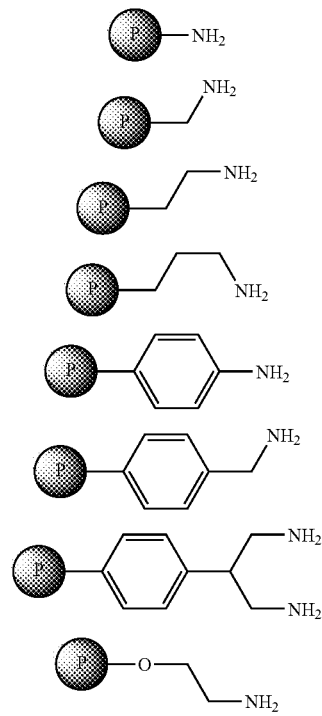

P = Polymer

Specific but nonlimiting examples of supports of the radical $R^{200}$ are Lichroprep $NH_2$ (TM/Merck) or aminomethylated polystyrene-divinylbenzene copolymer (Sigma-Aldrich).

Illustrative but nonlimiting examples of compounds of the formula I and II are:

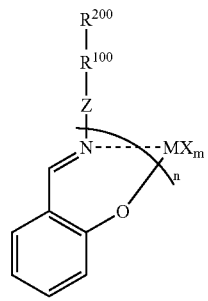

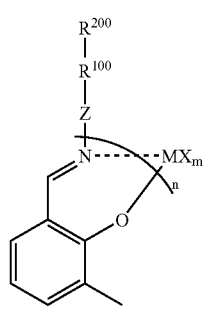
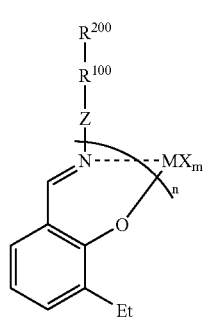
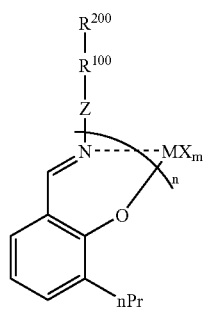
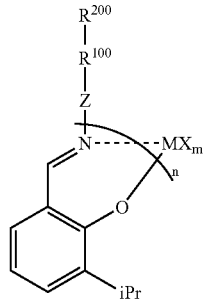
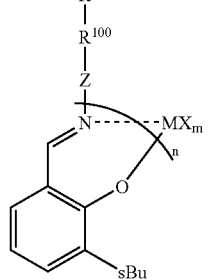
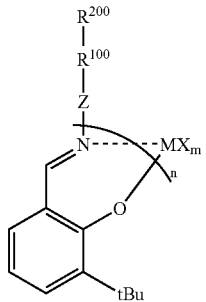
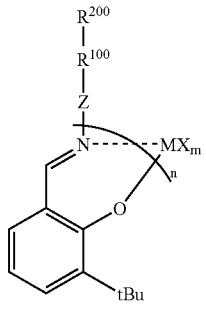
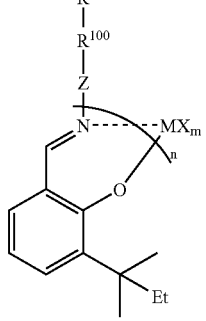
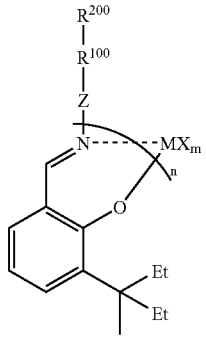
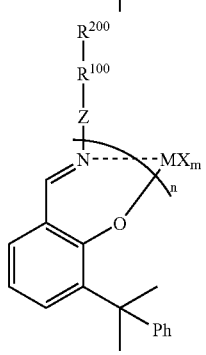

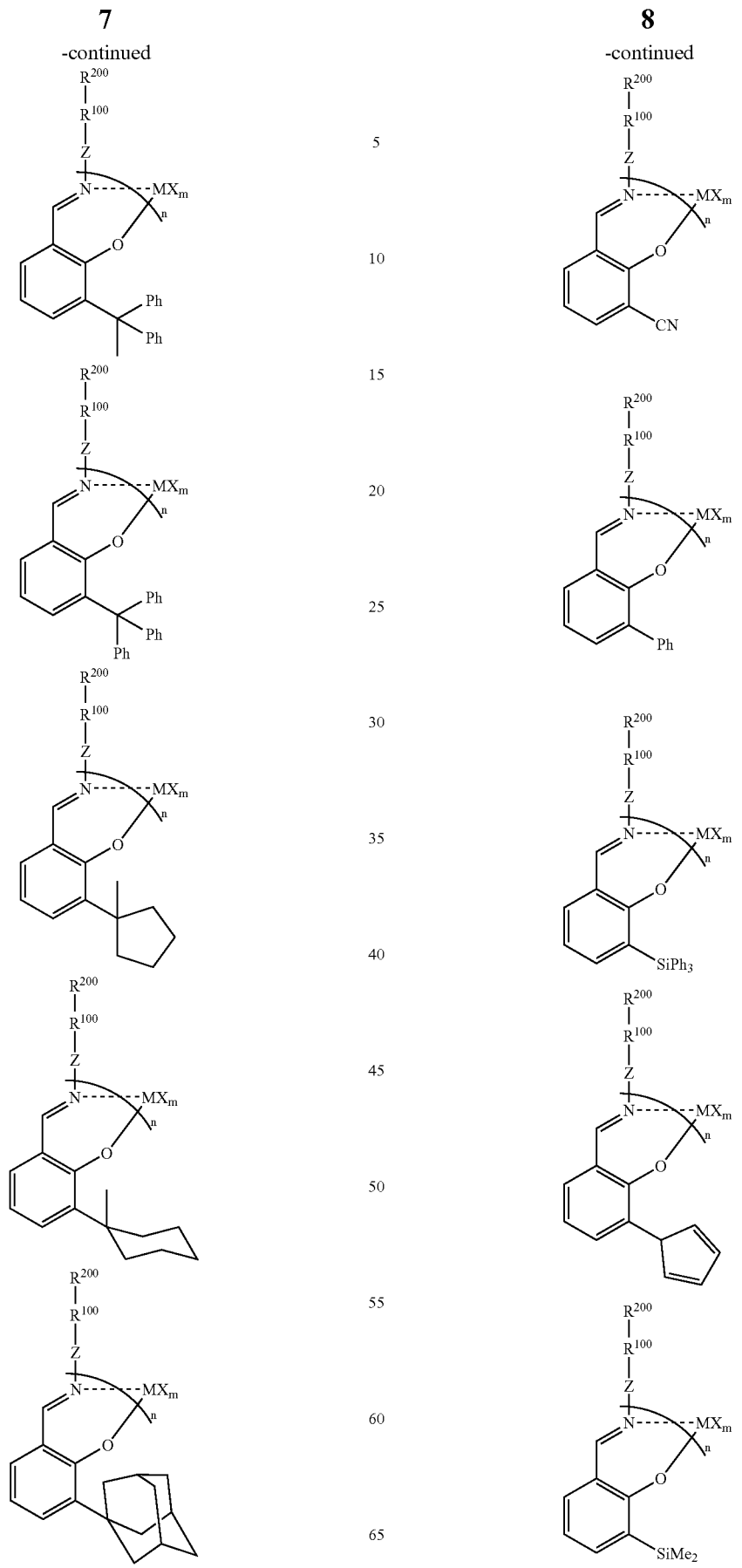

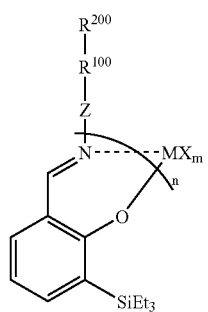
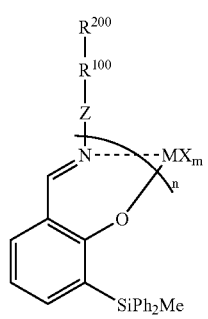
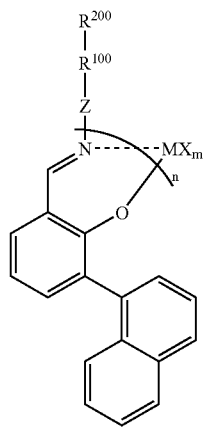
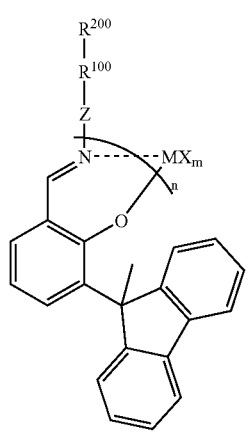
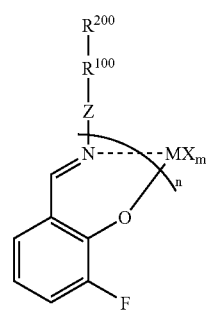
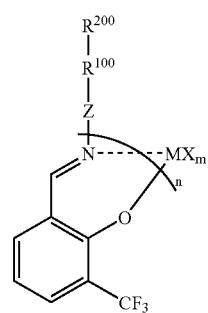
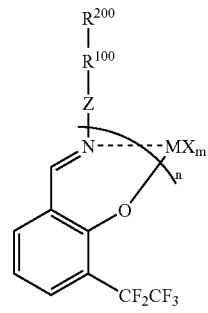
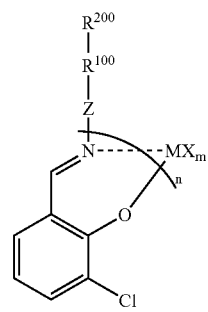
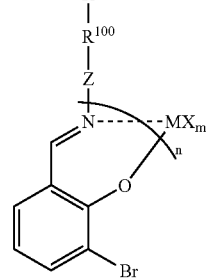

-continued
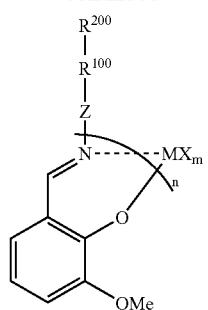
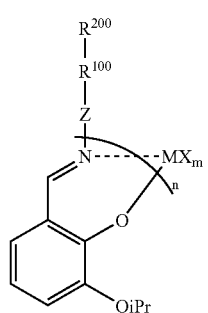
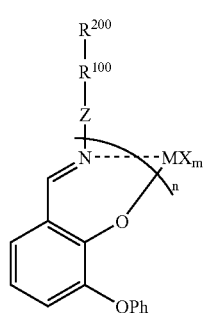
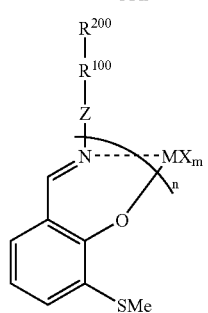
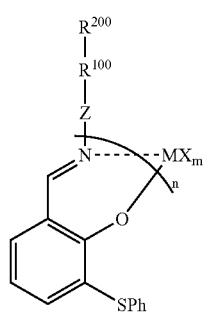
-continued
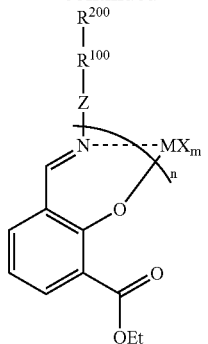
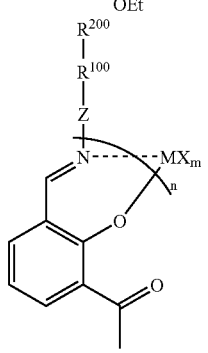
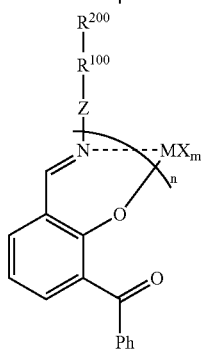
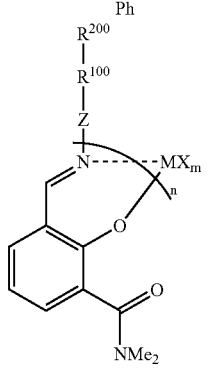
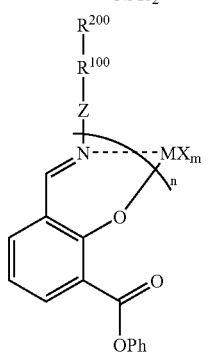

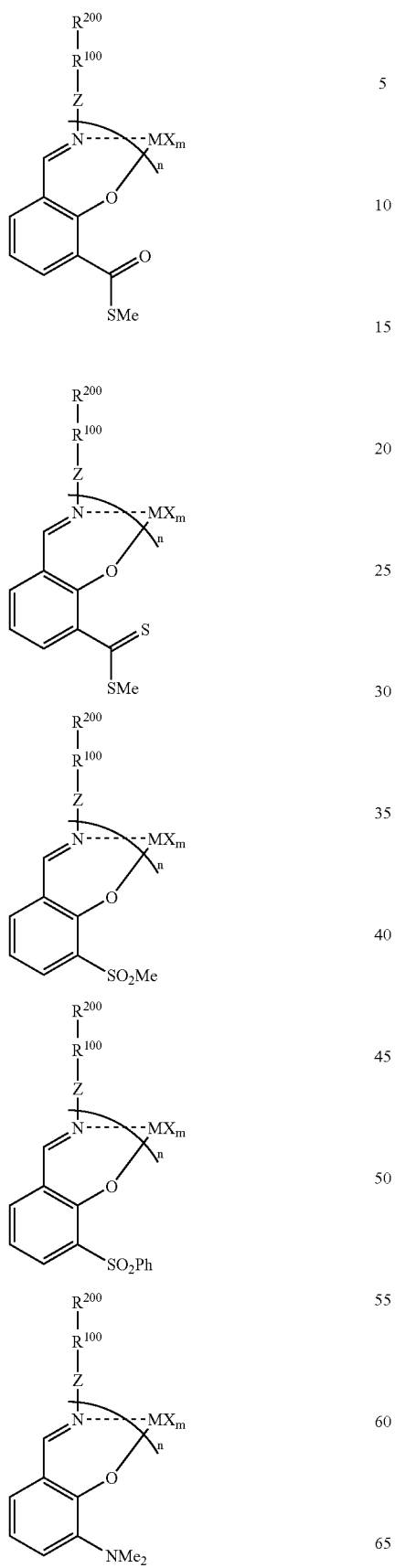

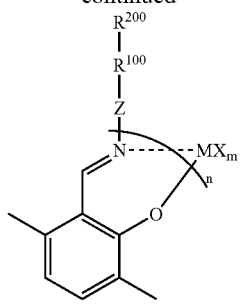
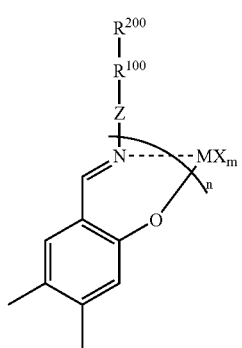
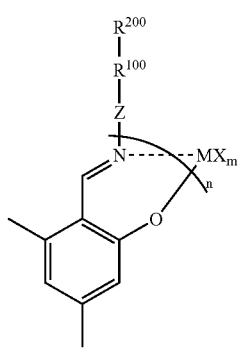
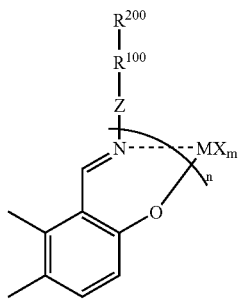
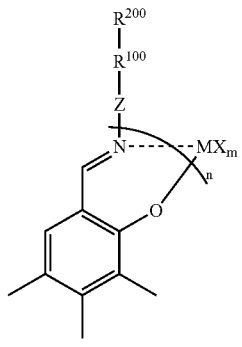
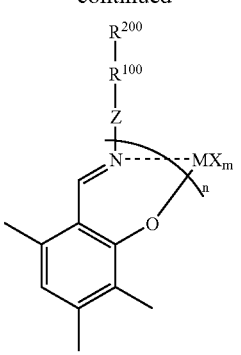
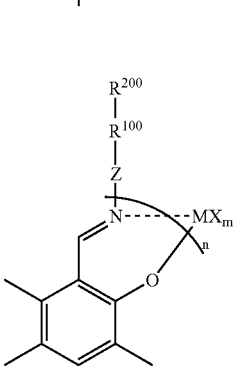
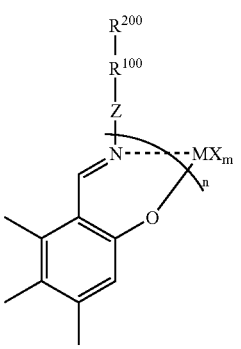
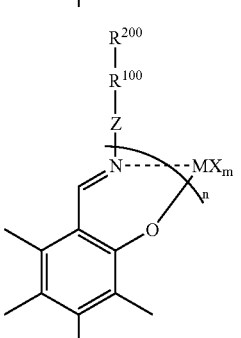
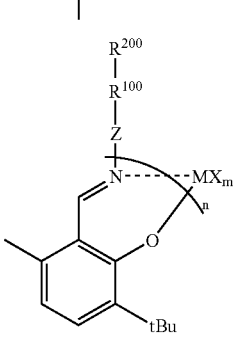

-continued
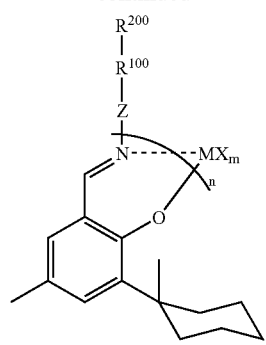
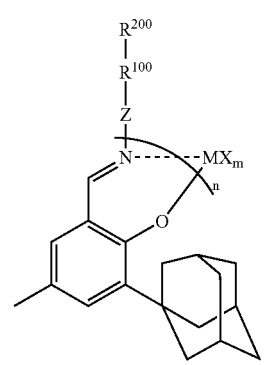
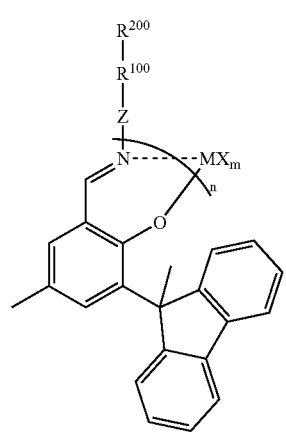
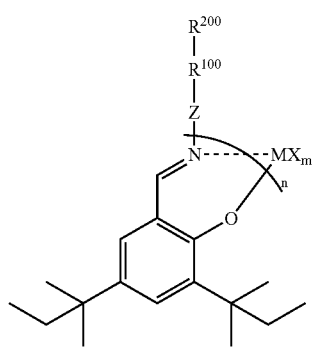
-continued
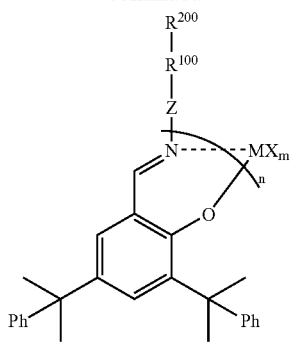
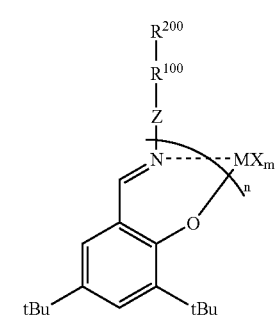
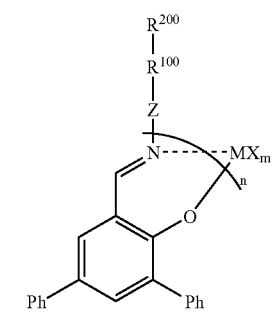
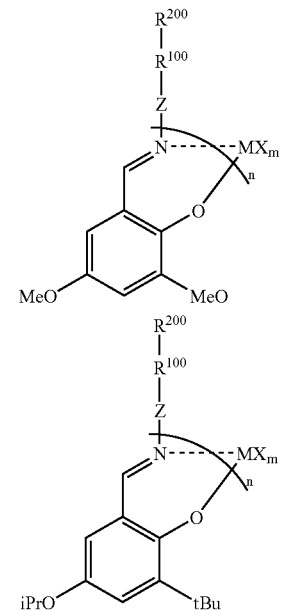

-continued
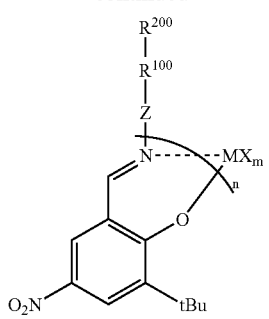
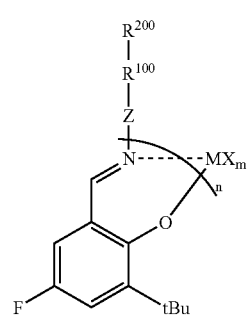
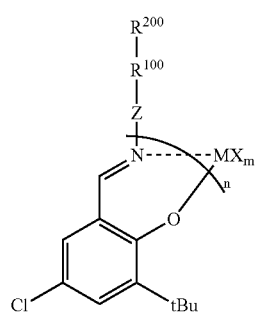
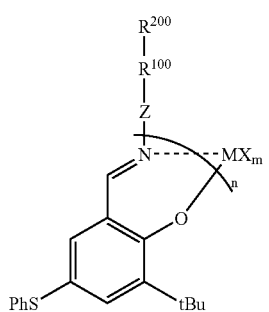
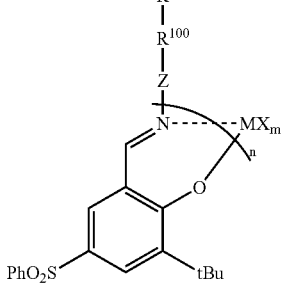
-continued
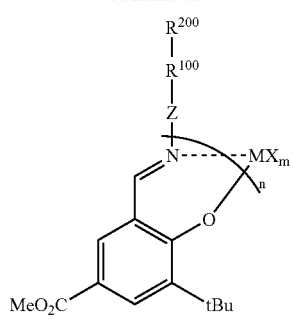
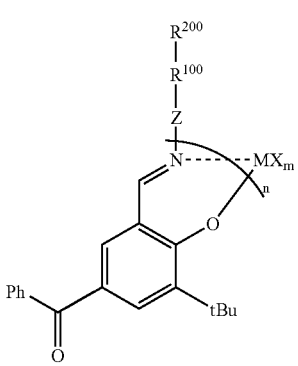
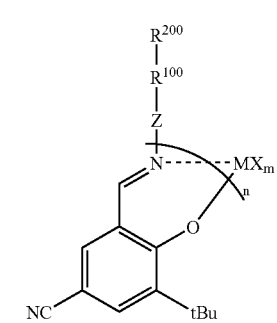
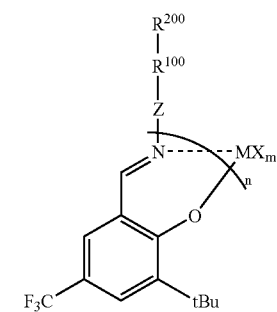
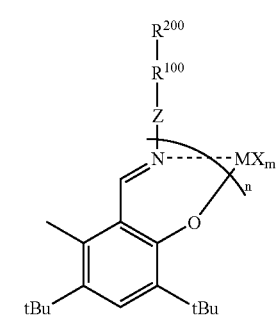

-continued
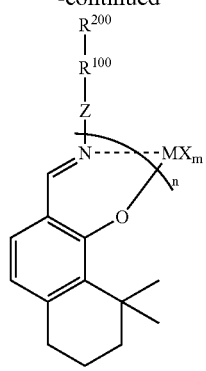
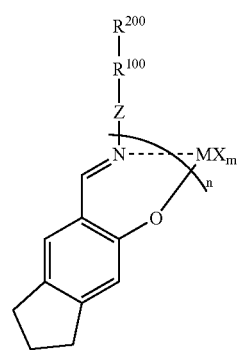
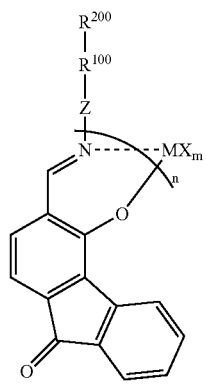
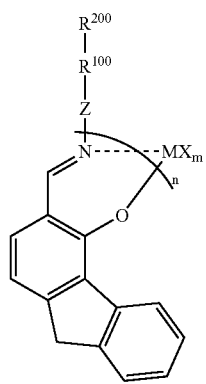
-continued
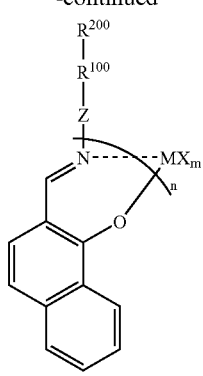
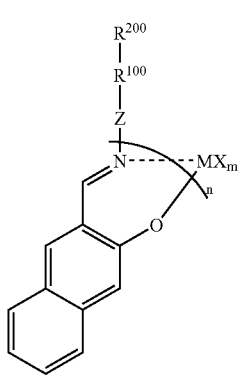
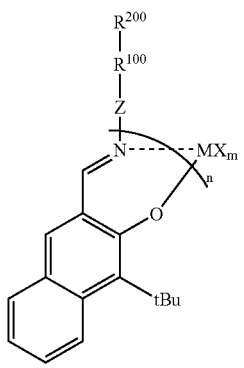
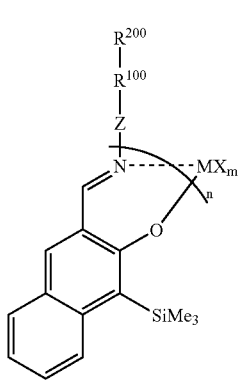

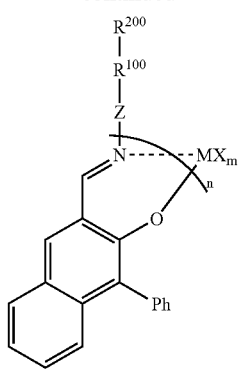
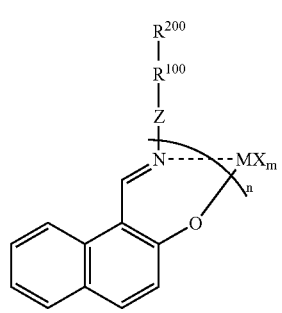
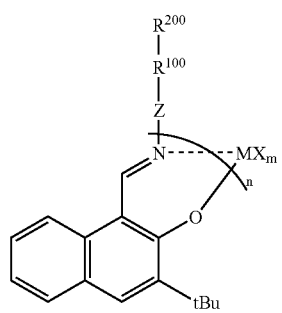
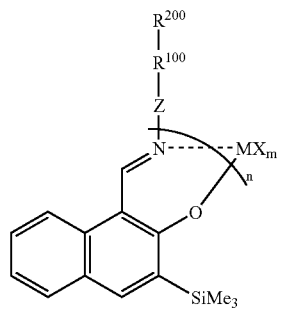
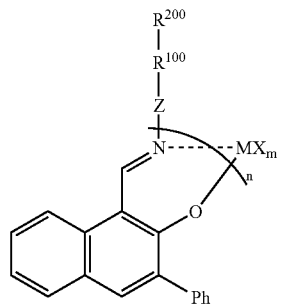
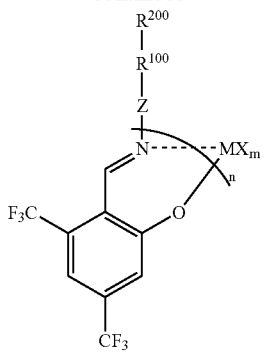
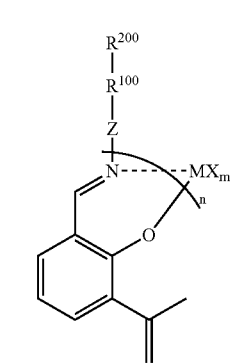
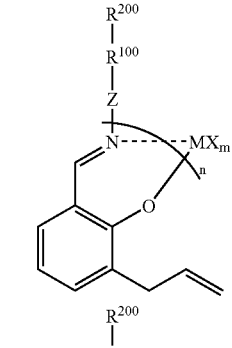
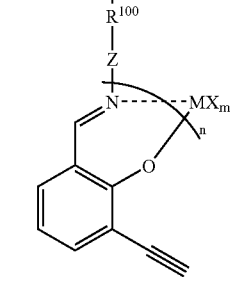
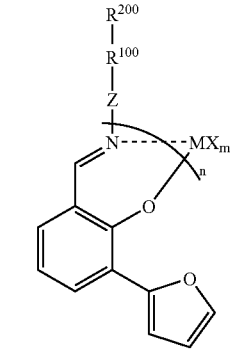

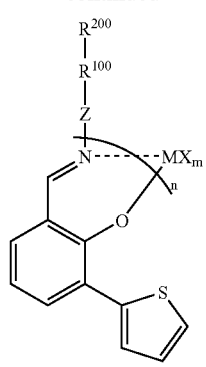
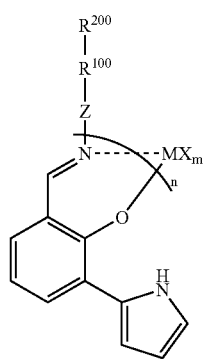
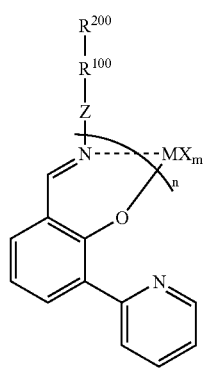
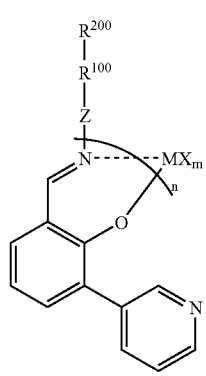
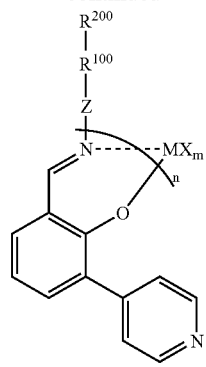
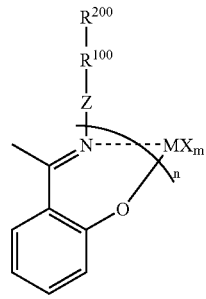
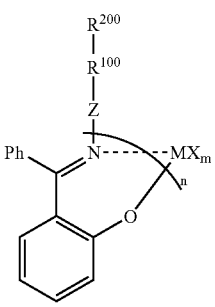
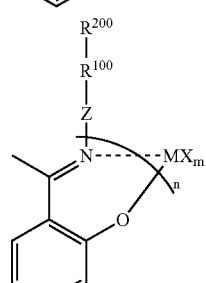
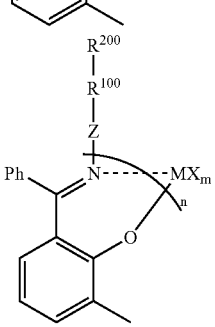

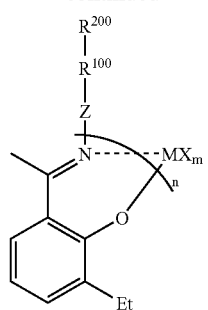
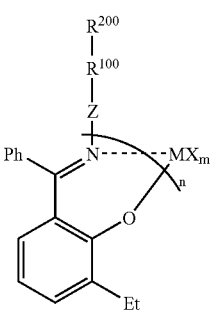
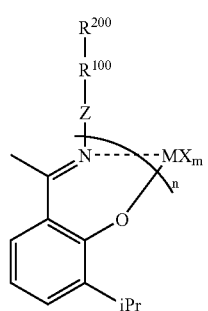
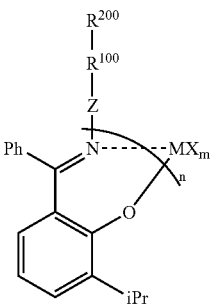
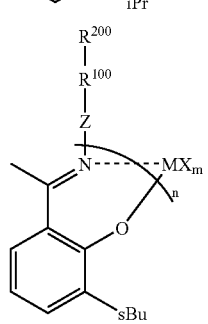
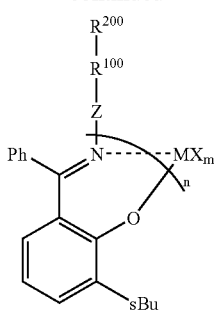
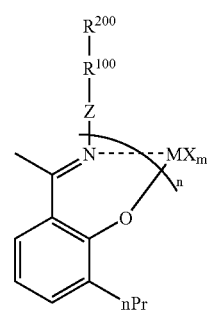
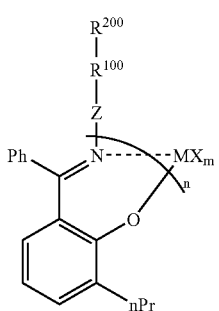
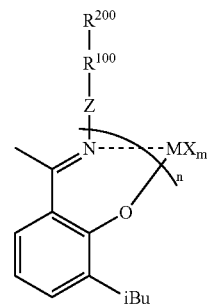
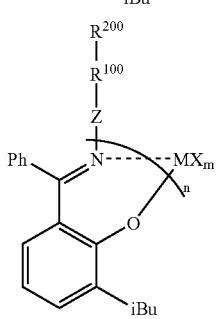

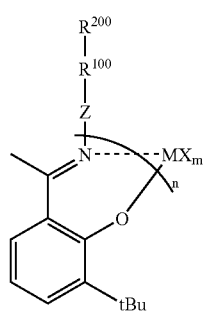
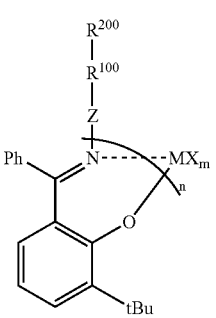
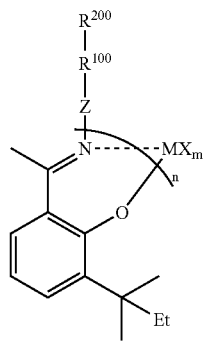
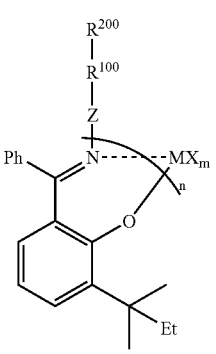
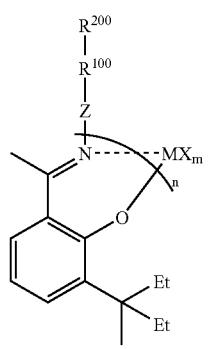
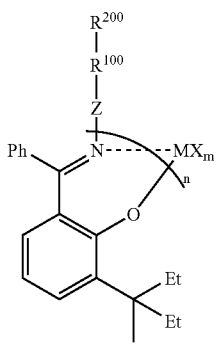
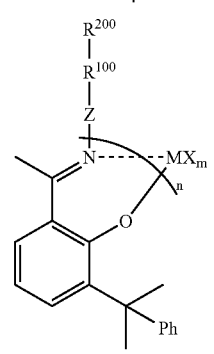
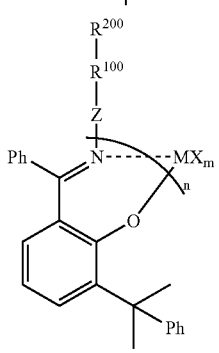
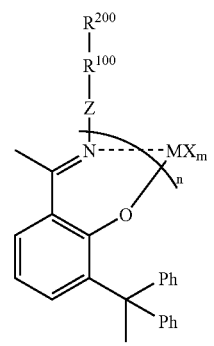
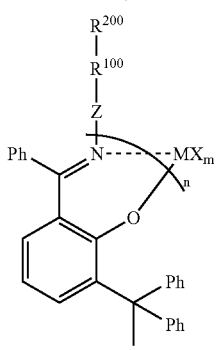

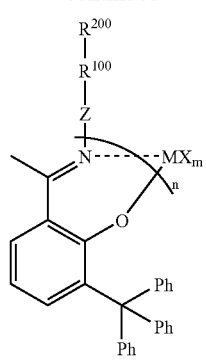
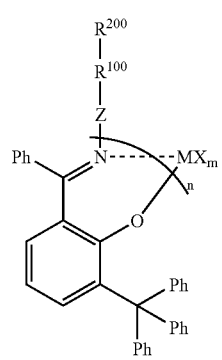
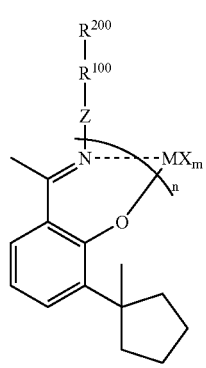
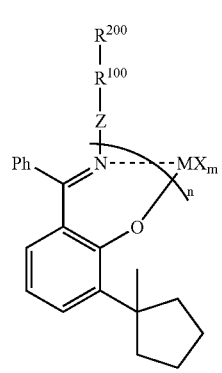
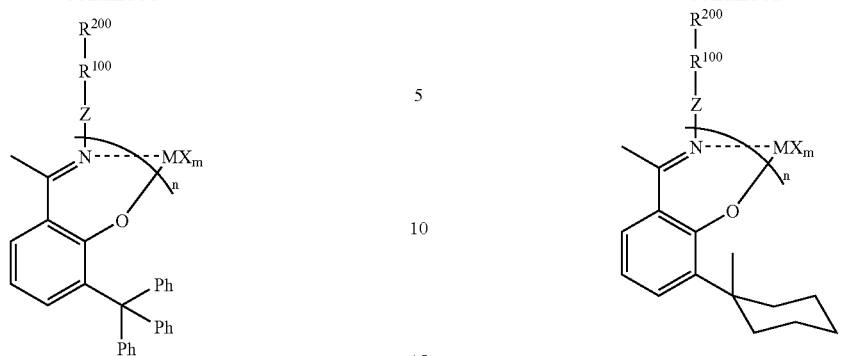
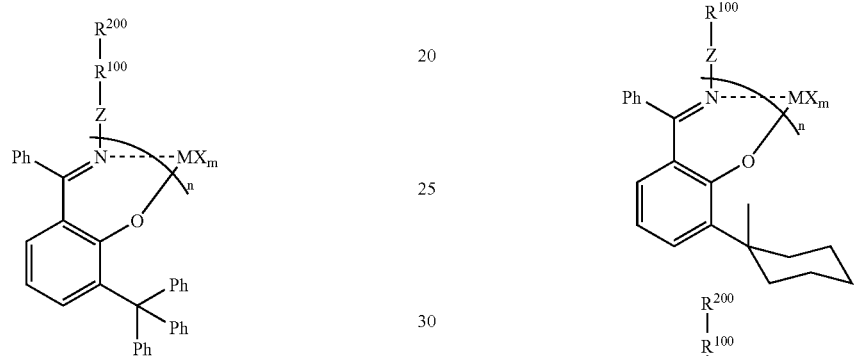
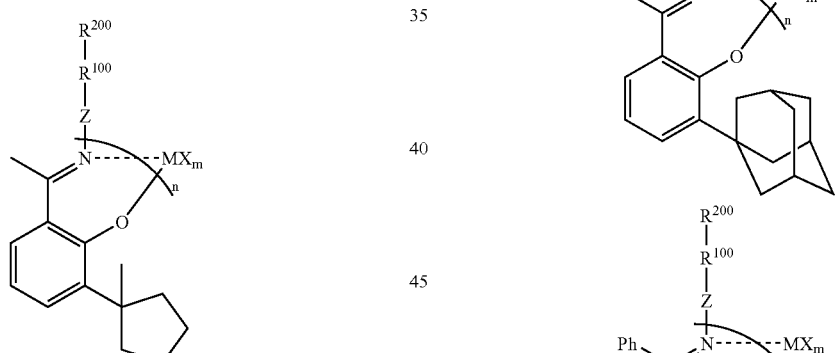
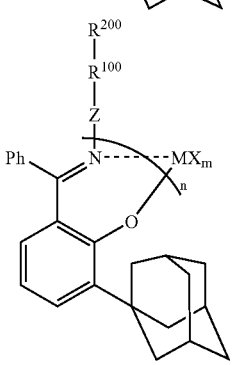
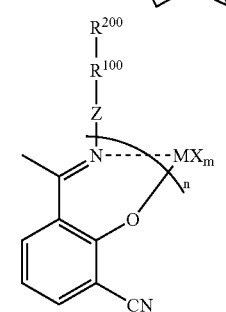

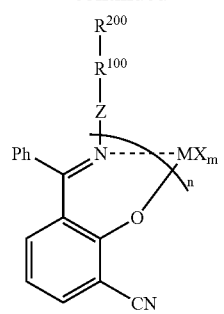
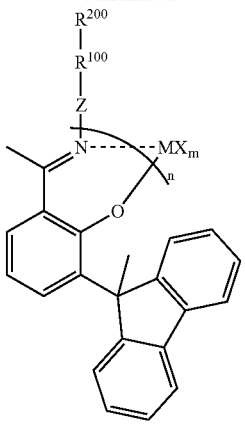
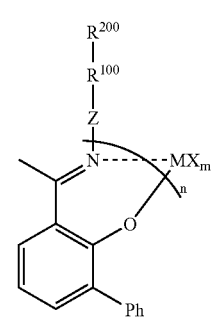
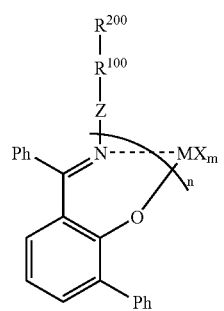
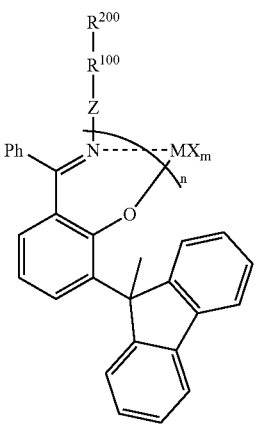
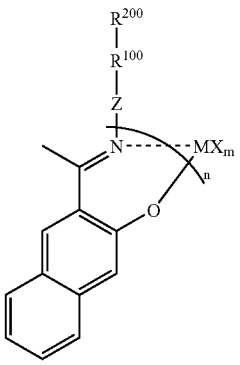
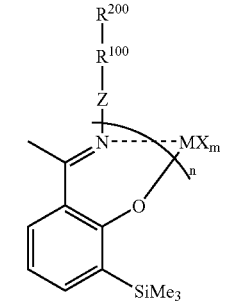
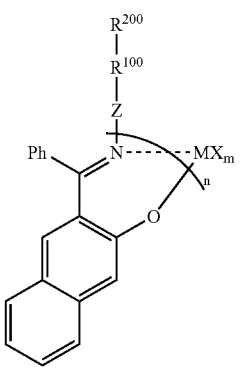
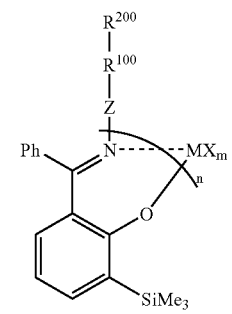

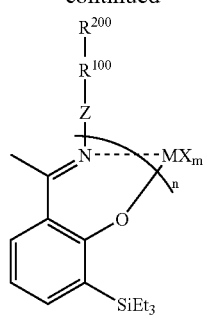
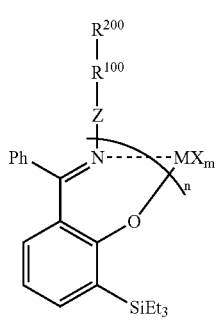
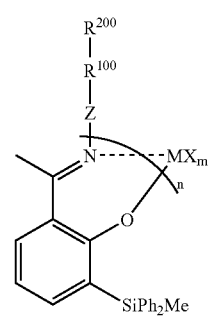
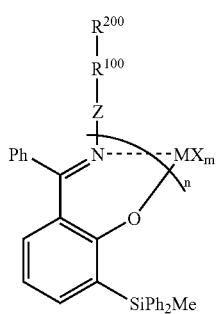
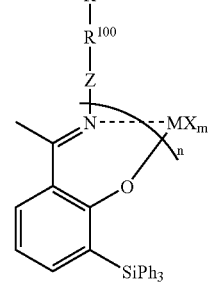
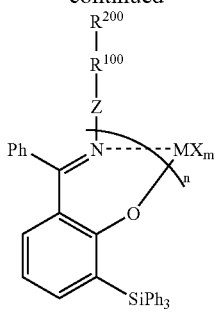
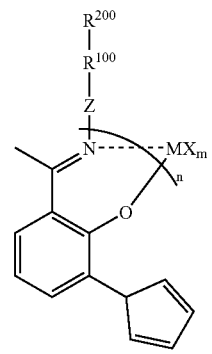
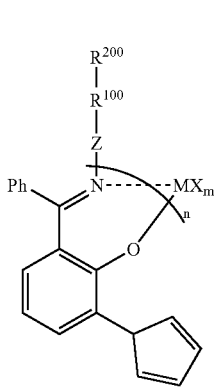
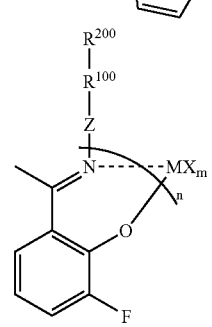
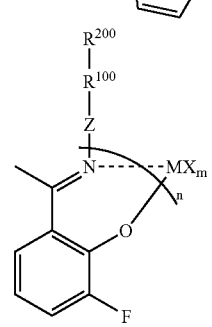

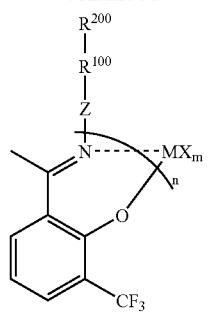
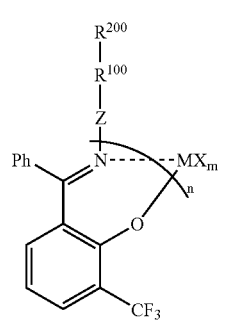
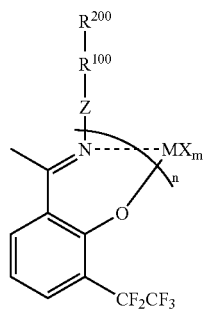
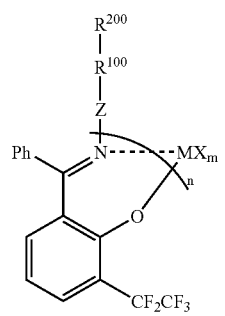
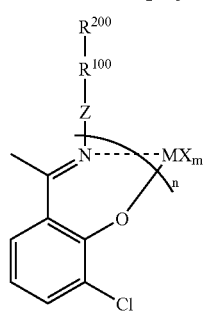
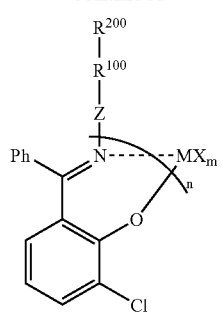
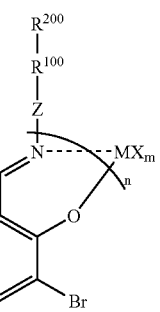
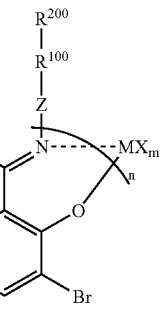
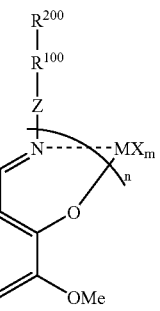
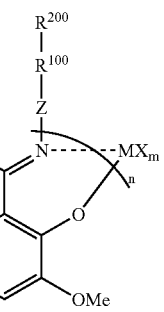

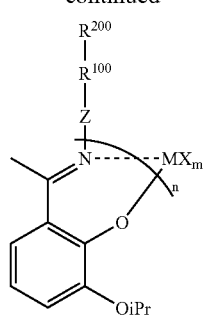
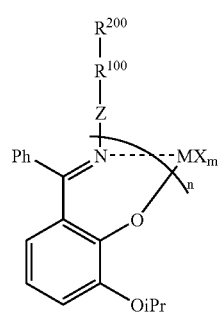
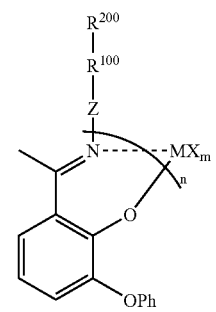
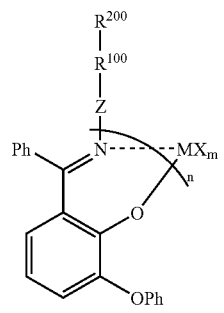
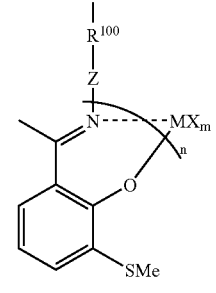
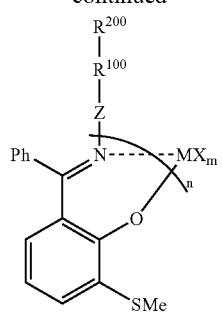
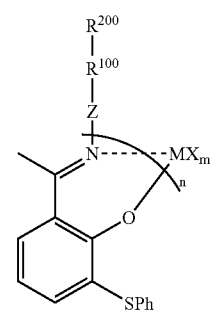
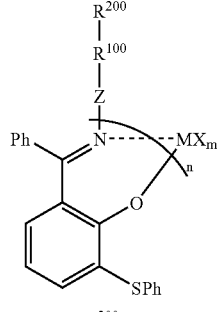
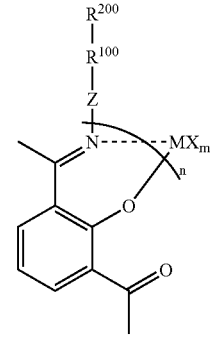
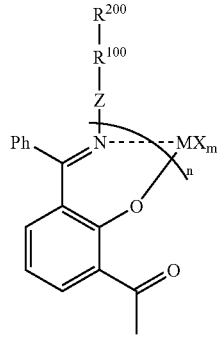

-continued
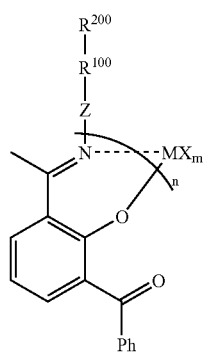
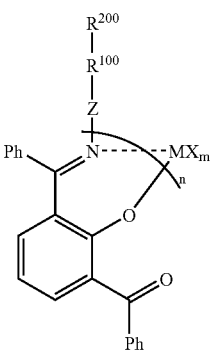
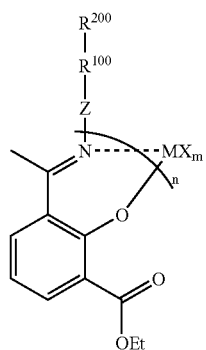
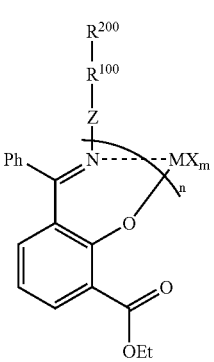
-continued
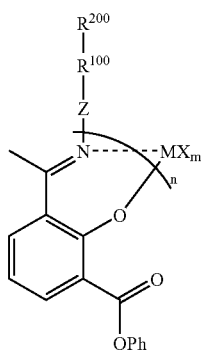
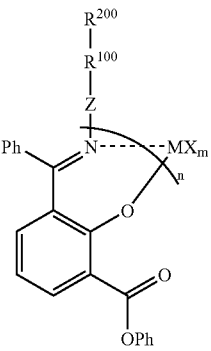
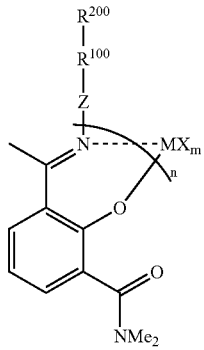
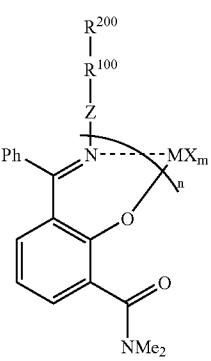

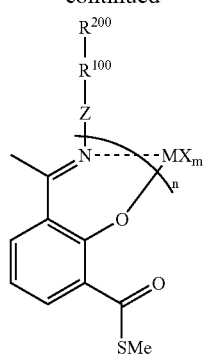
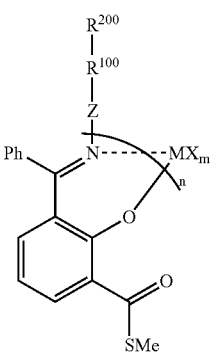
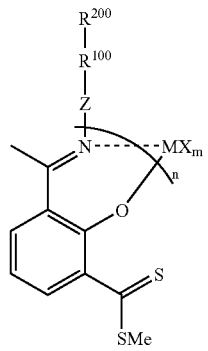
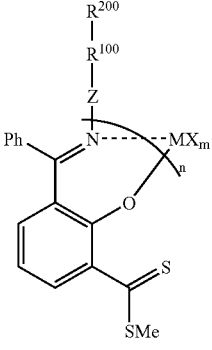
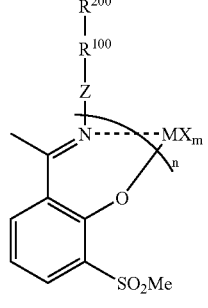
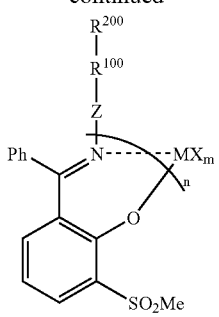
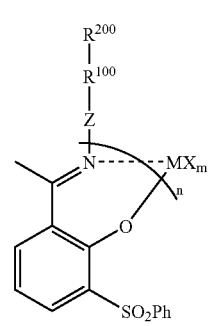
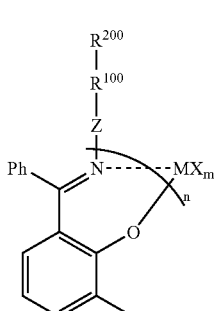
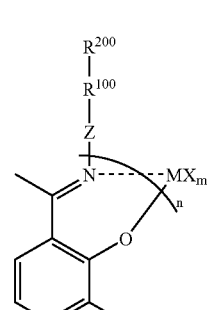
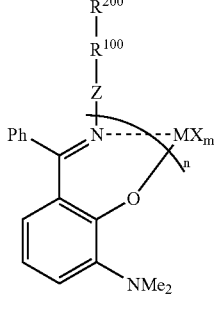

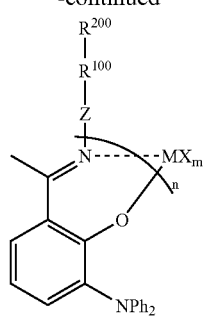
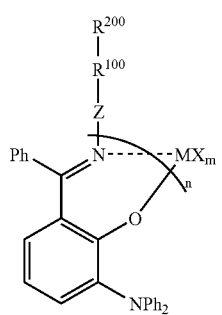
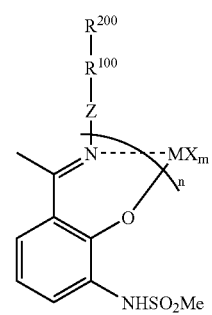
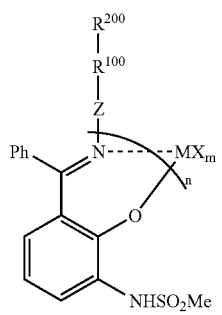
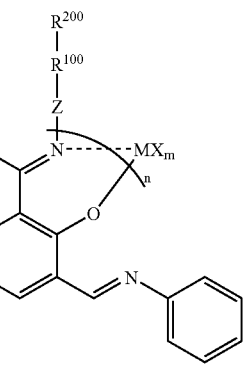
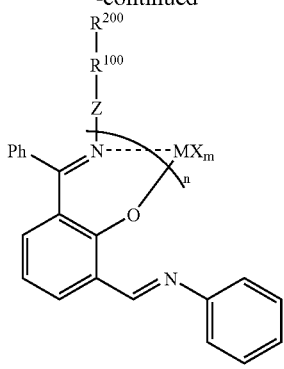
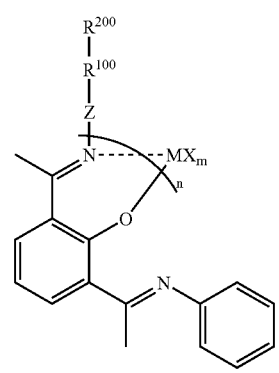
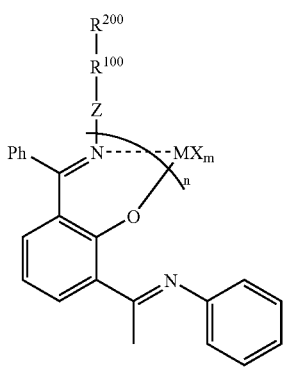

47
-continued
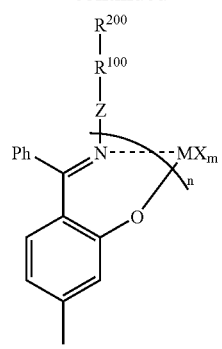
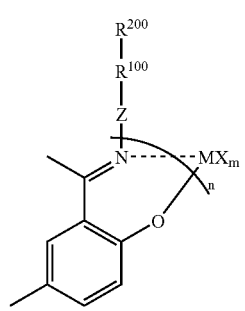
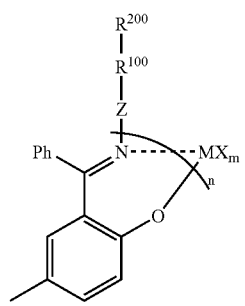
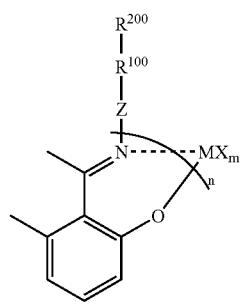
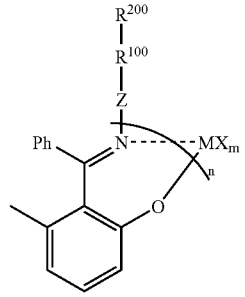
48
-continued
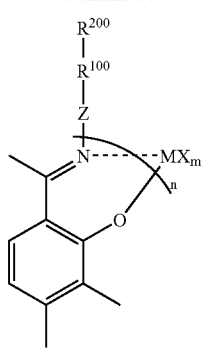
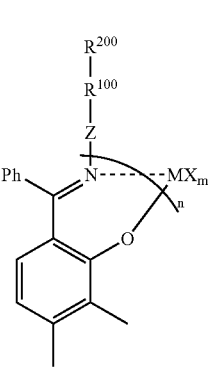
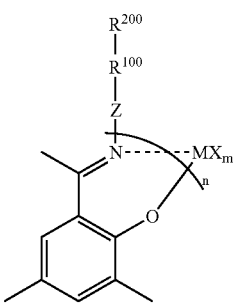
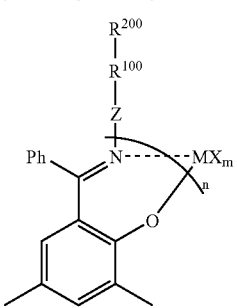
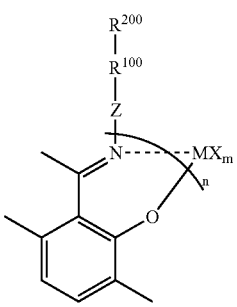

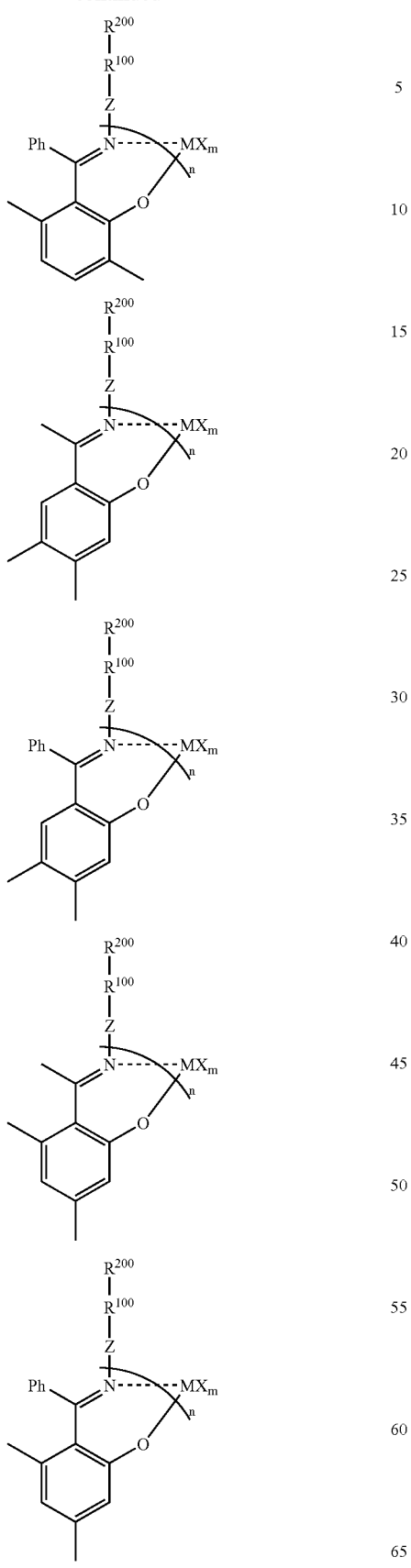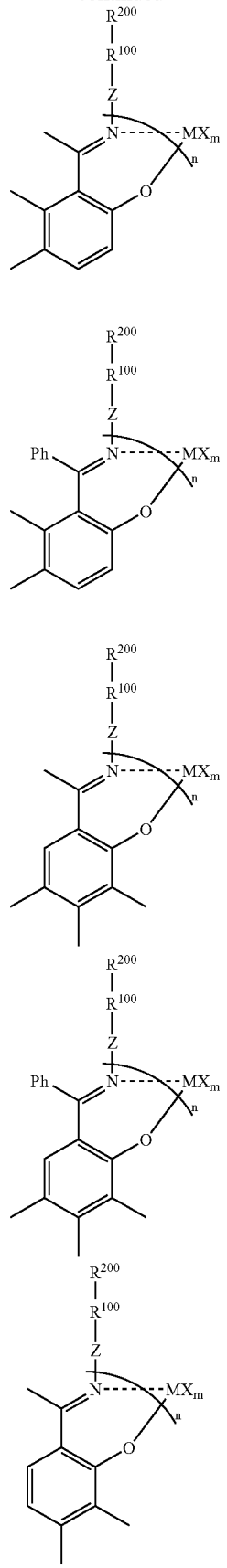

-continued
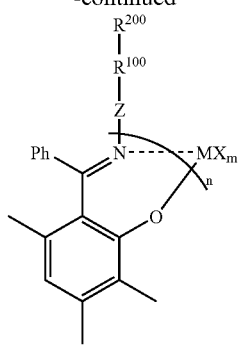
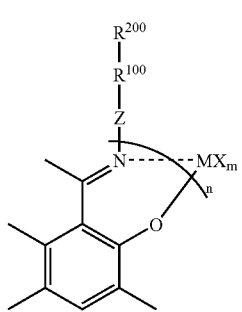
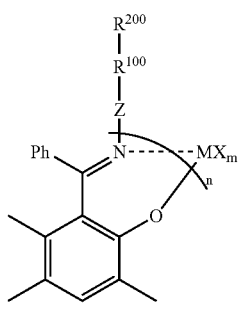
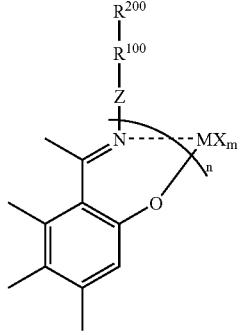
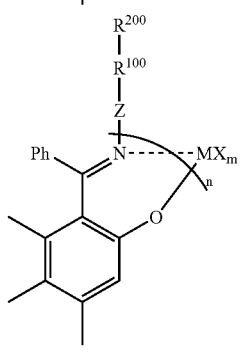
-continued
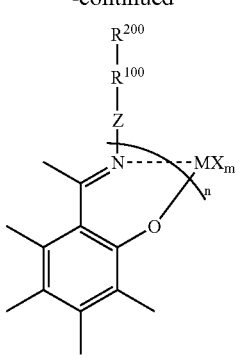
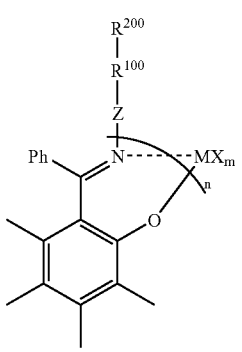
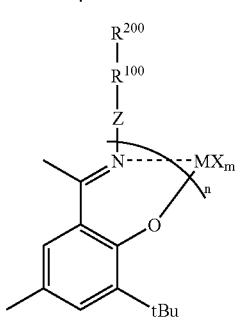
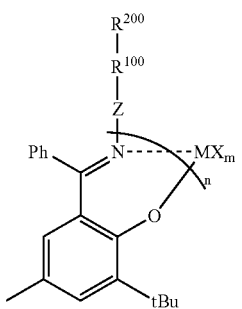
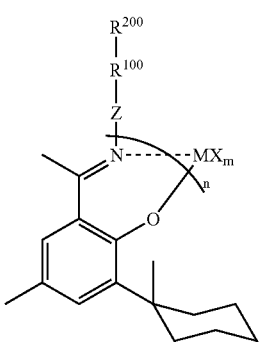

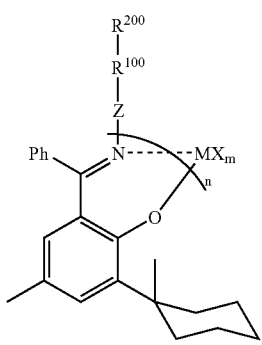
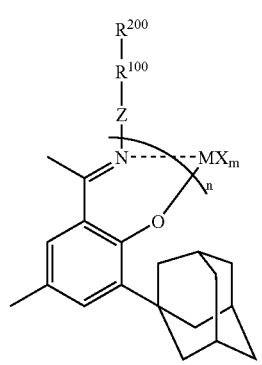
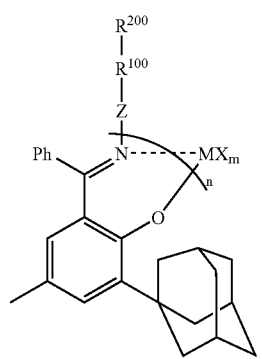
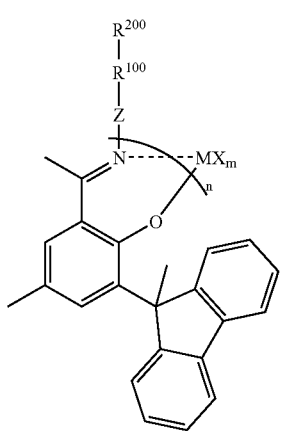
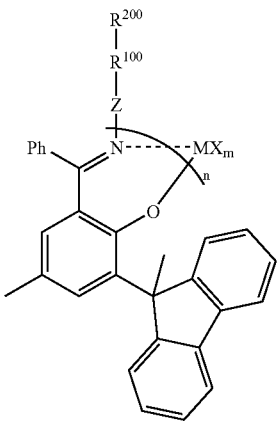
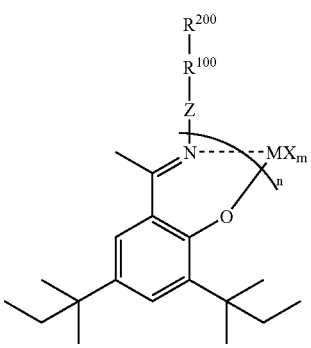
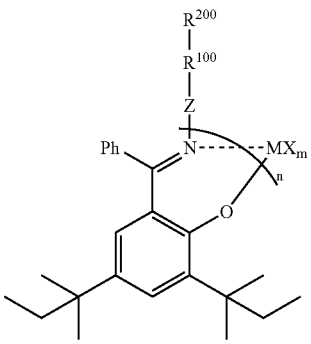
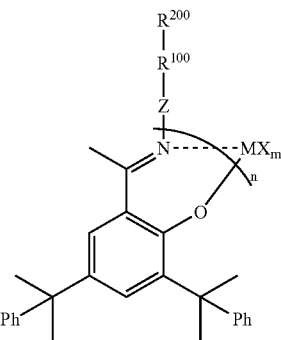

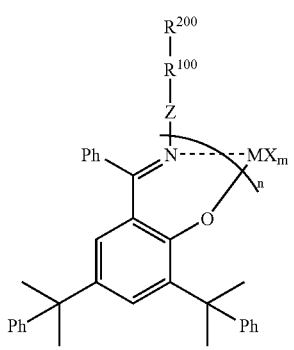
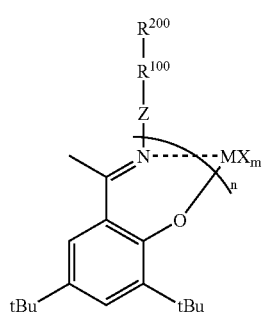
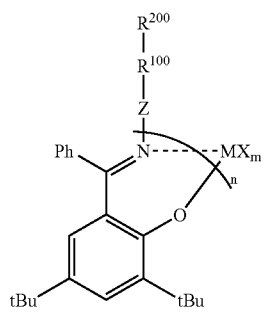
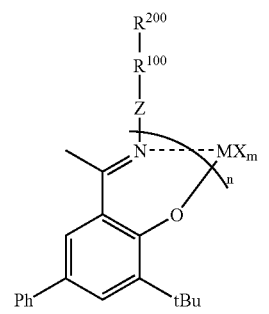
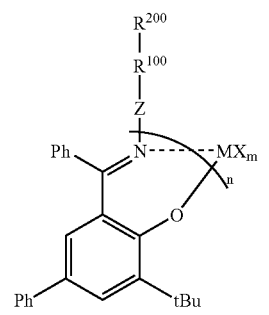
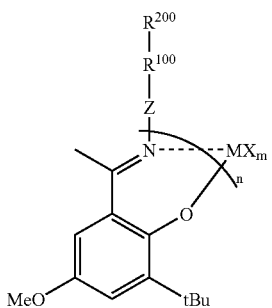
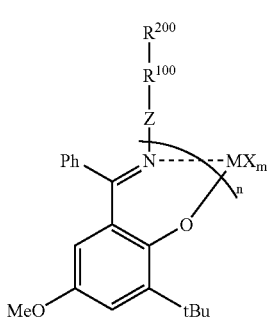
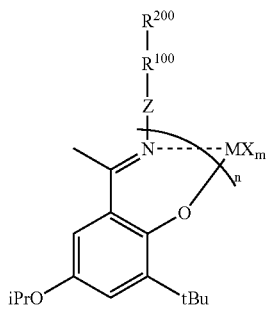
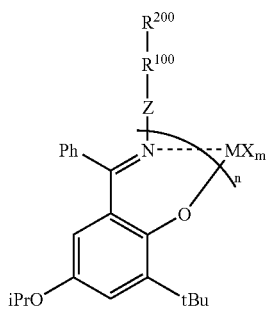
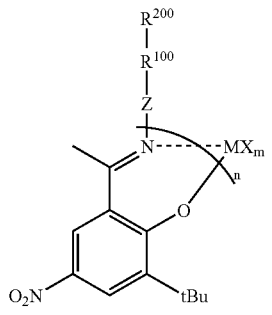

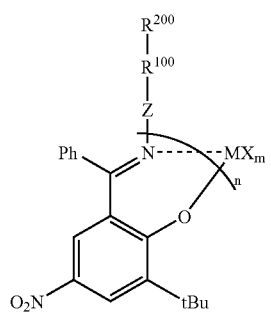
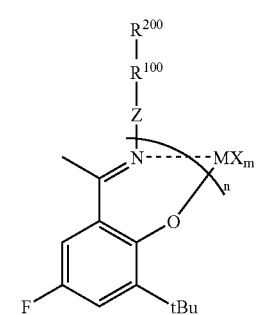
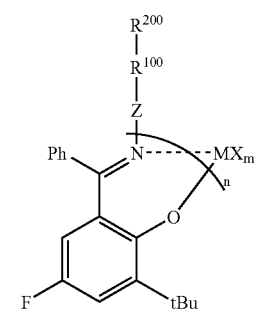
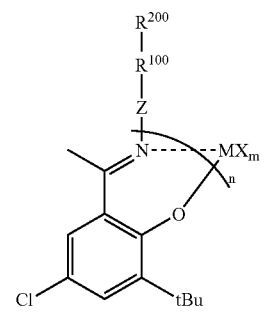
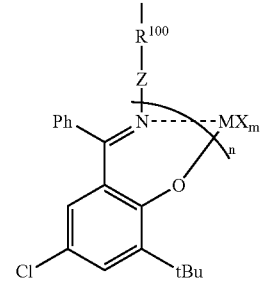
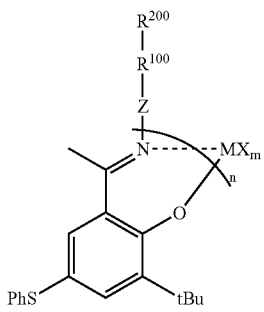
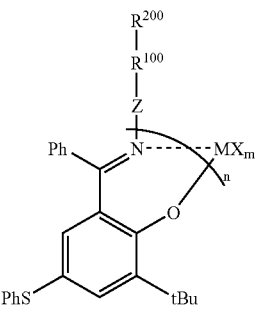
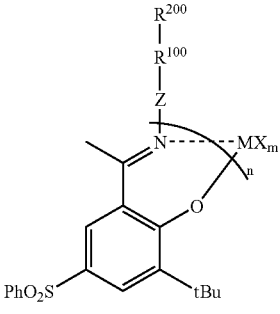
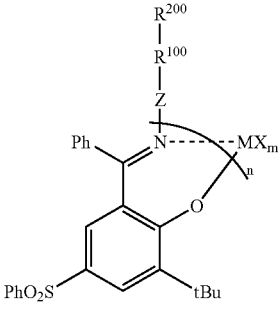
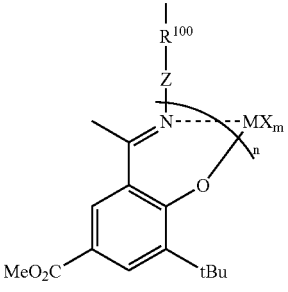

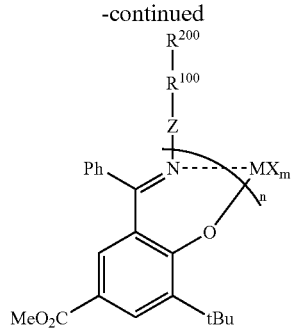
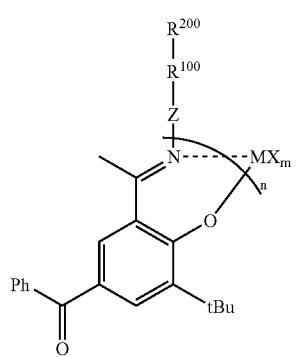
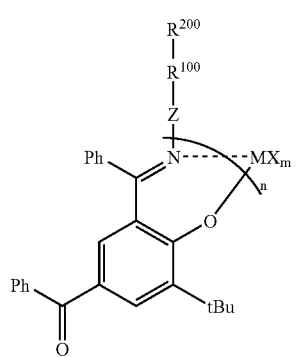
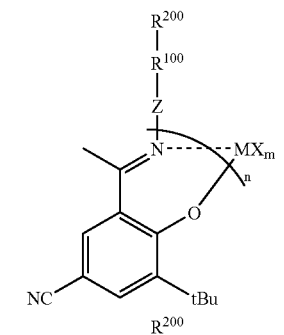
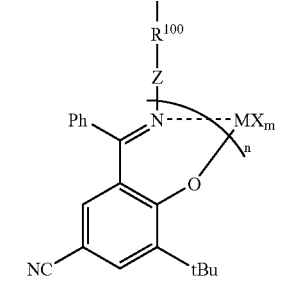
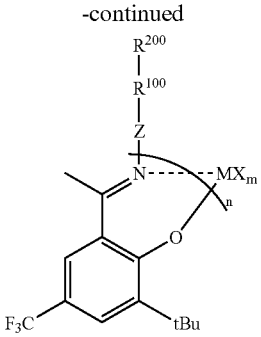
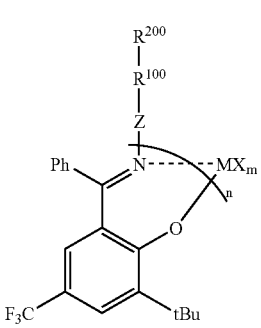
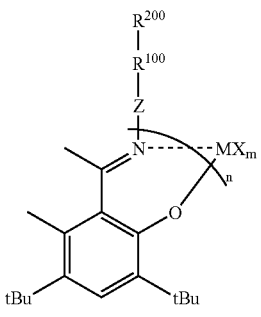
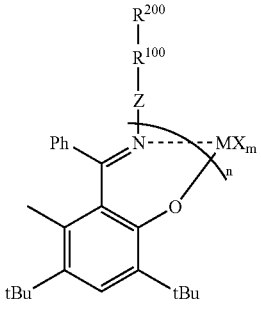
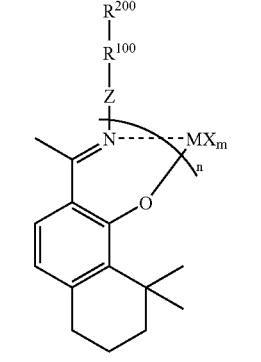

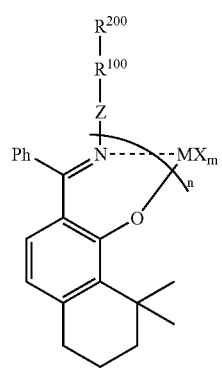
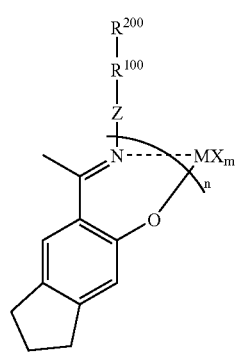
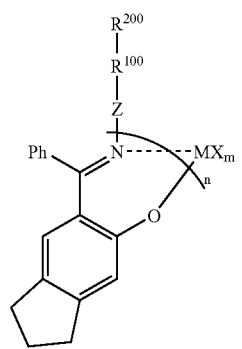
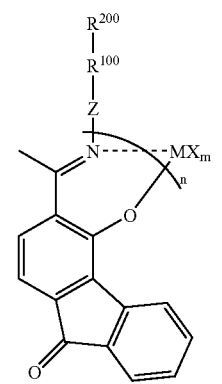
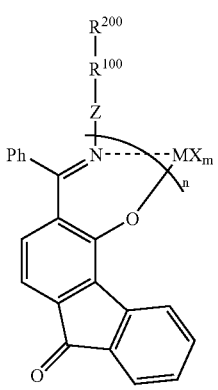
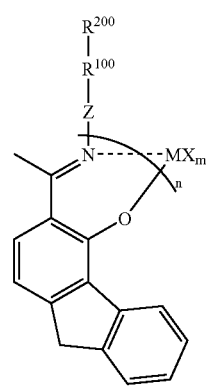
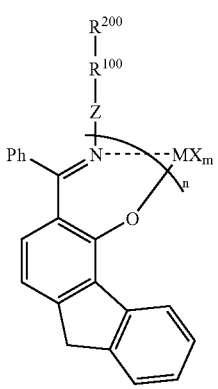
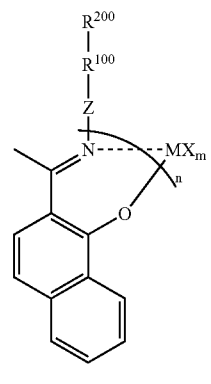

-continued
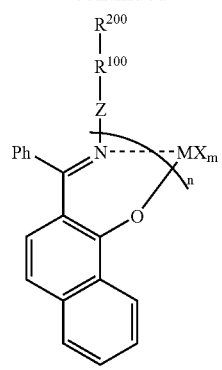
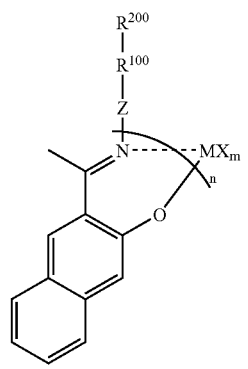
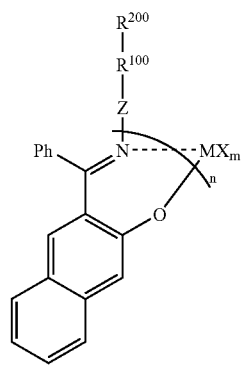
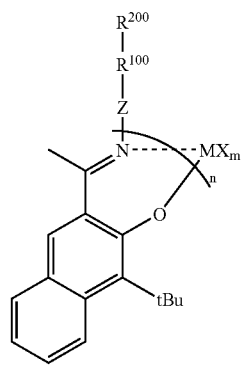
-continued
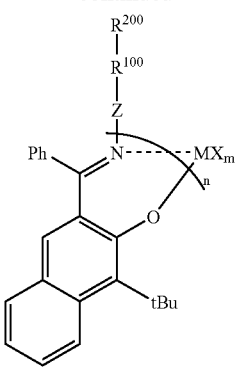
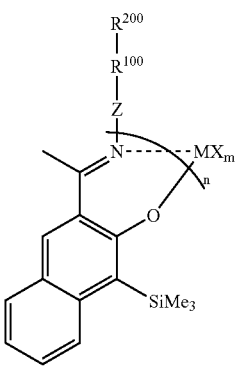
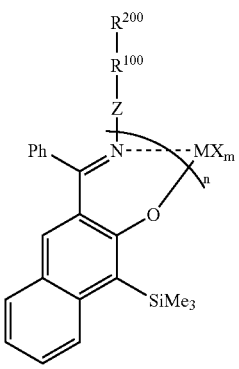
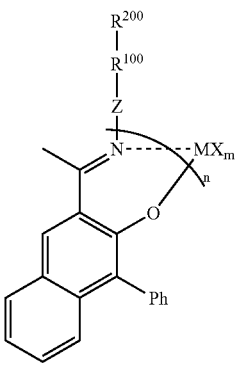

65
-continued
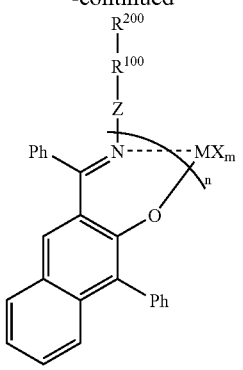
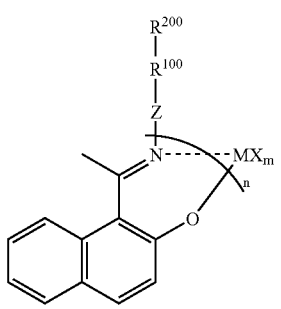
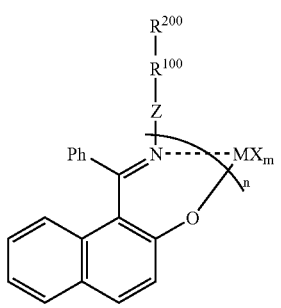
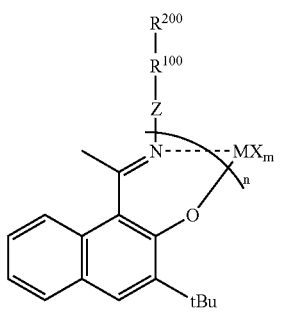
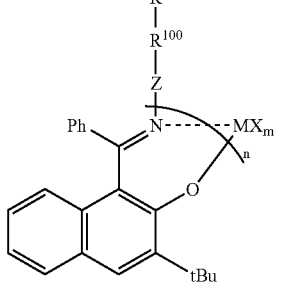
66
-continued
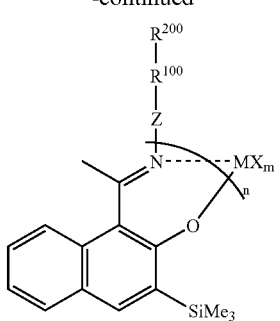
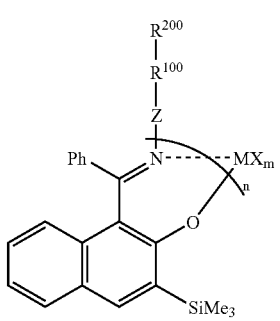
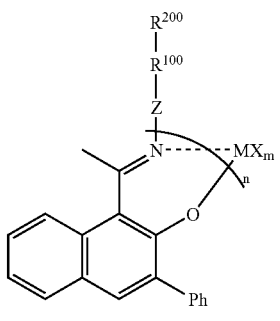
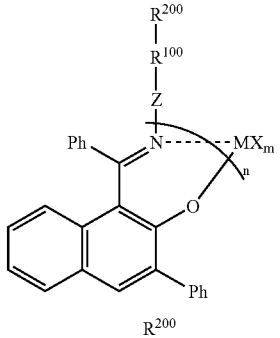
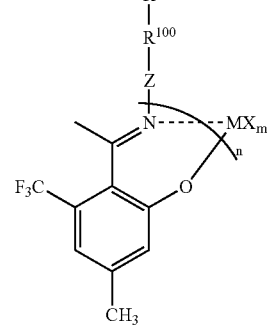

-continued
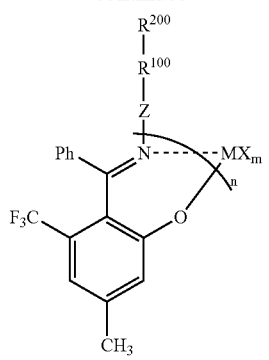
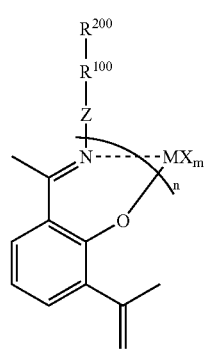
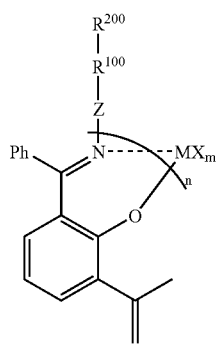
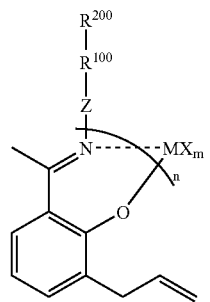
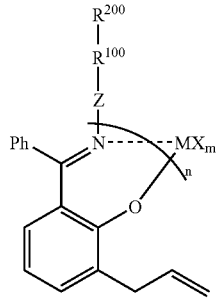
-continued
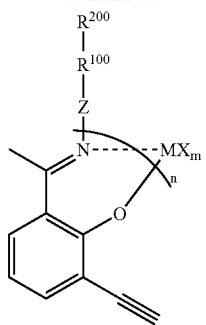
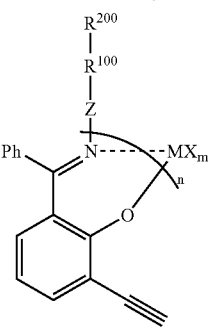
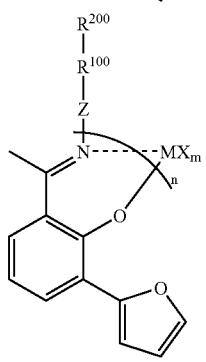
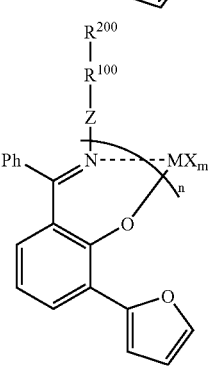
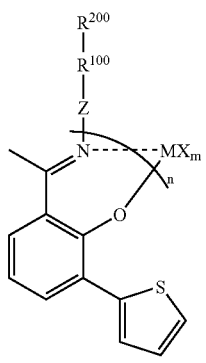

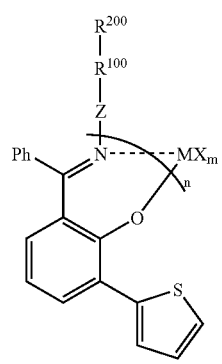
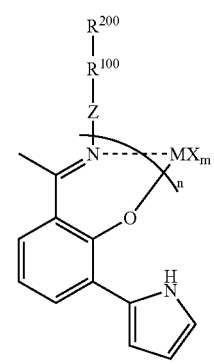
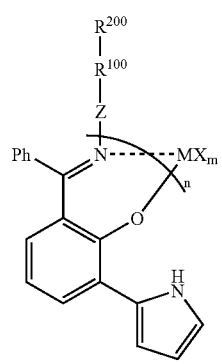
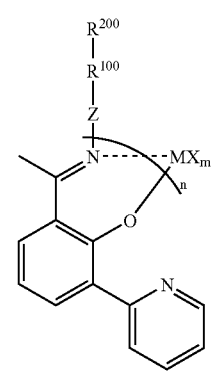
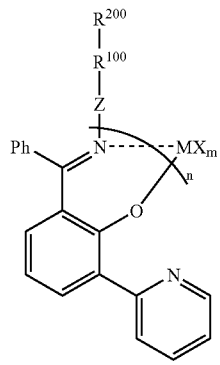
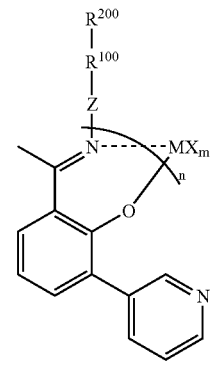
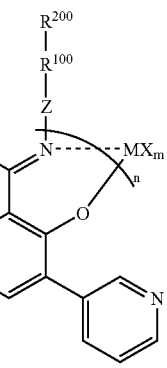
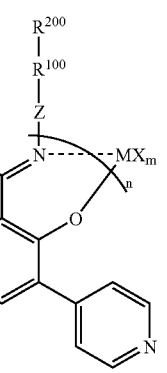

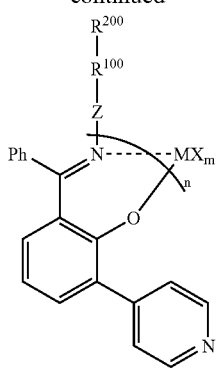

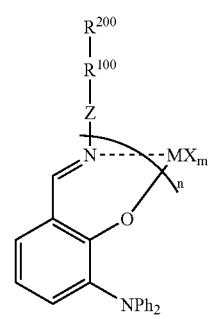

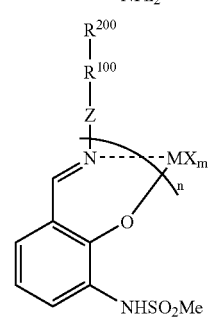

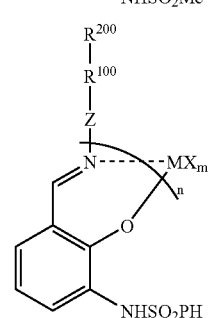

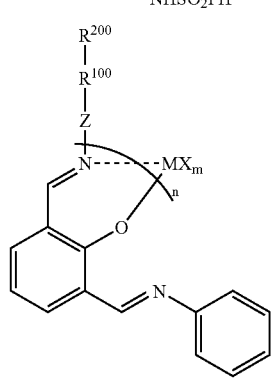

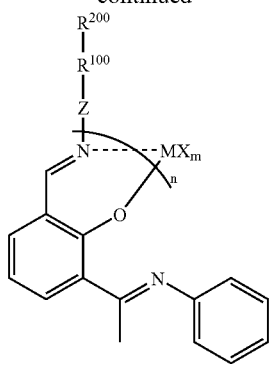

and also the above compounds in which the group Z is completely absent.

The present invention further provides metal compounds in which the zirconium fragment "zirconium dichloride" is replaced by zirconium monochloride mono(2,4-di-tert-butylphenoxide)
zirconium monochloride mono(2,6-di-tert-butylphenoxide)
zirconium monochloride mono(3,5-di-tert-butylphenoxide)
zirconium monochloride mono(2,6-di-sec-butylphenoxide)
zirconium monochloride mono(2,4-dimethylphenoxide)
zirconium monochloride mono(2,3-dimethylphenoxide)
zirconium monochloride mono(2,5-dimethylphenoxide)
zirconium monochloride mono(2,6-dimethylphenoxide)
zirconium monochloride mono(3,4-dimethylphenoxide)
zirconium monochloride mono(3,5-dimethylphenoxide)
zirconium monochloride monophenoxide
zirconium monochloride mono(2-methylphenoxide)
zirconium monochloride mono(3-methylphenoxide)
zirconium monochloride mono(4-methylphenoxide)
zirconium monochloride mono(2-ethylphenoxide)
zirconium monochloride mono(3-ethylphenoxide)
zirconium monochloride mono(4-ethylphenoxide)
zirconium monochloride mono(2-sec-butyl phenoxide)
zirconium monochioride mono(2-tert-butylphenoxide)
zirconium monochloride mono(3-tert-butylphenoxide)
zirconium monochloride mono(4-sec-butylphenoxide)
zirconium monochloride mono(4-tert-butylphenoxide)
zirconium monochloride mono(2-isopropyl-5-methylphenoxide)
zirconium monochloride mono(4-isopropyl-3-methylphenoxide)
zirconium monochloride mono(5-isopropyl-2-methylphenoxide)
zirconium monochloride mono(5-isopropyl-3-methylphenoxide)
zirconium monochloride mono(2,4-bis(2-methyl-2-butyl) phenoxide)
zirconium monochloride mono(2,6-di-tert-butyl-4-methylphenoxide)
zirconium monochloride mono(4-nonyl phenoxide)
zirconium monochloride mono(1-naphthoxide)
zirconium monochloride mono(2-naphthoxide)
zirconium monochloride mono(2-phenylphenoxide)
zirconium monochloride mono(tert-butoxide)
zirconium monochloride mono(N-methylanilide)

zirconium monochloride mono(2-tert-butylanilide)
zirconium monochloride mono(tert-butylamide)
zirconium monochloride mono(diisopropylamide)
zirconium monochloride monomethyl
zirconium monochloride monobenzyl The present invention also provides a process for preparing the novel chemical compounds of the formulae (I) and (II). A possible reaction sequence is shown by way of example for the compounds of the formula (I) in the following diagram. This reaction sequence applies analogously to the compounds of the formula (II):

$M^2$ is an element of group I or II of the Periodic Table of the Elements, preferably lithium, sodium, potassium or magnesium, very particularly preferably lithium or sodium, and $M^3$ is an element of group 13, 14, 15 or 16 of the Periodic Table of the Elements, preferably nitrogen, phosphorus, very particularly preferably nitrogen.

For this purpose, one or more compounds of the formula (III), which may be suspended in a solvent or can be in pure form, are reacted with one or more compounds of the

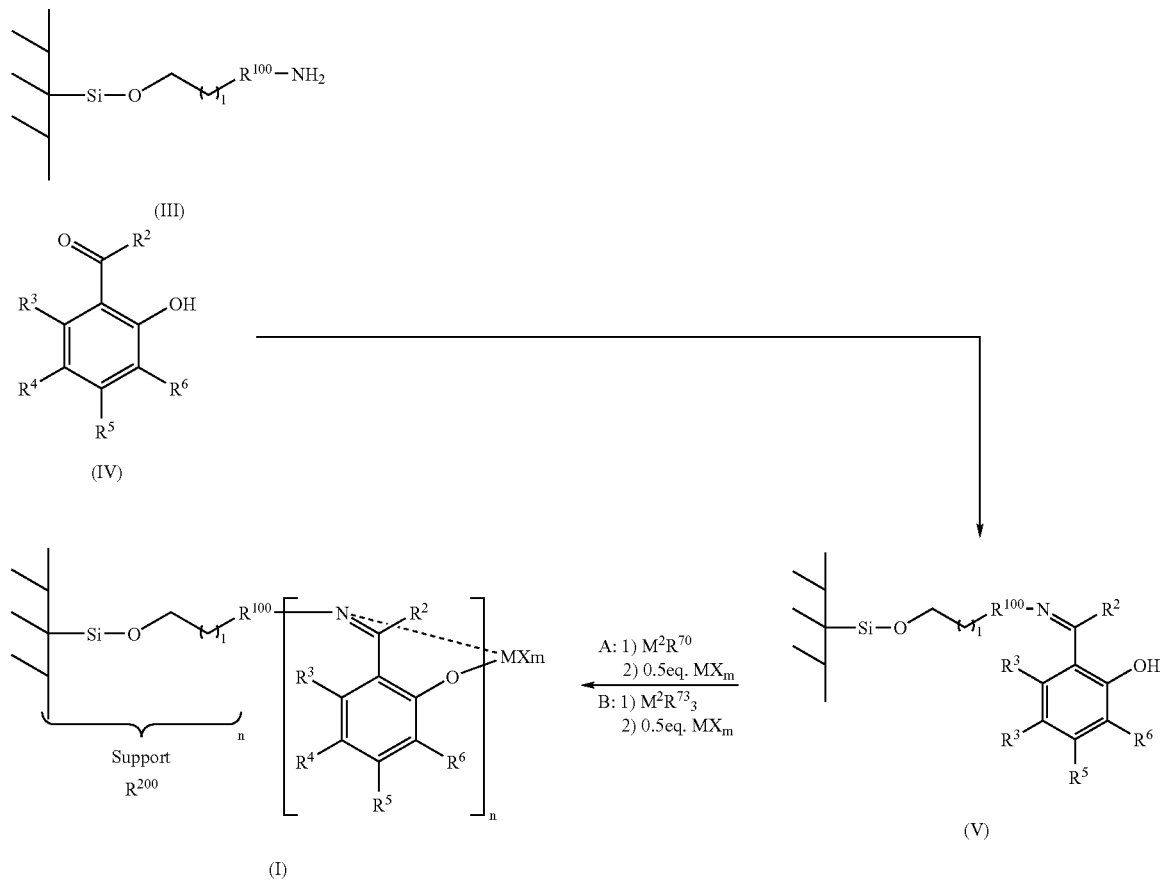

In this reaction sequence, M, $R^2$, $R^3$, $R^5$, X, m, n, i are as defined above. In addition:

$R^{70}$ is a hydrogen atom or a $C_1$–$C_{20}$ group, and $R^{71}$ is a halogen atom such as chlorine, bromine, fluorine, or $Si(R^{10})_3$, where the radicals $R^{10}$ are identical or different and are each $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl and preferred alkyloxy groups are MeO, EtO and ButO groups, and $R^{73}$ is a hydrogen atom or a linear or branched $C_1$–$C_{12}$-alkyl group, preferably methyl, ethyl, n-butyl, n-hexyl, isopropyl, isobutyl, isopentyl, cyclohexyl, cyclopentyl or octyl, particularly preferably methyl, ethyl, isopropyl or cyclohexyl, or a halogen atom or $C_5$–$C_{18}$-heteroaryl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, and formula (IV), which can likewise be dissolved or suspended in a solvent or can be in pure form. Solvents used are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers such as diethyl ether, methyl tert-butyl ether, dimethoxyethane, diisopropyl ether, di-n-butyl ether, anisole, methanol, ethanol, isopropanol and butanol or mixtures of these. The addition can be carried out over a period of from 1 minute to 96 hours. Preference is given to addition over a period of from 100 minutes to 36 hours. The temperature of the initial charge during the addition is from –100° C. to 200° C. Preference is given to temperatures in the range from –80° C. to 150° C. Particular preference is given to temperatures in the range from 20° C. to 150° C.

The temperature is selected so that at least one of the reactants is liquid. The subsequent reaction temperature is in a preferred temperature range from 20° C. to 150° C. Furthermore, the reaction can be carried out at atmospheric pressure, but can also be carried out at superatmospheric pressure, though this requires appropriate reactors. The stoichiometric ratio in which the compounds of the formulae (III) and (IV) are combined is from 1:1000 to 1:0.01, based on the amount of compounds of the formula (III) used. Preference is given to a stoichiometric ratio between compounds of the formula (III) and (IV), based on the amount of compounds of the formula (III) used, of from 1:100 to 1:0.1. Particular preference is given to a virtually stoichiometric reaction based on the compounds of the formulae (III) and (IV). A compound of the formula (V) results.

Illustrative but nonlimiting examples of compounds of the formula (IV) which can be used for the purposes of the invention are:

3,5-di-tert-butyl-2-hydroxybenzaldehyde, 1-[3,5-di(tert-butyl)-2-hydroxyphenyl]ethan-1-one, 2-hydroxybenzophenone, 2-hydroxybenzaldehyde, 1-[-2-hydroxyphenyl]ethan-1-one, 3,5-diisopropyl-2-hydroxybenzaldehyde, 3,5-ditrimethylsilyl-2-hydroxybenzaldehyde, 3,5-dimethyl-2-hydroxybenzaldehyde, 3,5-diethyl-2-hydroxybenzaldehyde, 3,5-di-n-propyl-2-hydroxybenzaldehyde, 3,5-di-n-butyl-2-hydroxybenzaldehyde, 3,5-diphenyl-2-hydroxybenzaldehyde, 3,5-ditolyl-2-hydroxybenzaldehyde, 3,5-dinaphthyl-2-hydroxybenzaldehyde, 3,5-diadamantyl-2-hydroxybenzaldehyde, 3,5-dinorbornyl-2-hydroxybenzaldehyde, 3,5-difluoro-2-hydroxybenzaldehyde, 3,5 dichloro-2-hydroxybenzaldehyde, 4,6-diisopropyl-2-hydroxybenzaldehyde, 4,6-ditrimethylsilyl-2-hydroxybenzaldehyde, 4,6-dimethyl-2-hydroxybenzaldehyde, 4,6-diethyl-2-hydroxybenzaldehyde, 4,6-di-n-propyl-2-hydroxybenzaldehyde, 4,6-di-n-butyl-2-hydroxybenzaldehyde, 4,6-di-phenyl-2-hydroxybenzaldehyde, 4,6-ditolyl-2-hydroxybenzaldehyde, 4,6-dinaphthyl-2-hydroxybenzaldehyde, 4,6-diadamantyl-2-hydroxybenzaldehyde, 4,6-dinorbornyl-2-hydroxybenzaldehyde, 4,6-difluoro-2-hydroxybenzaldehyde, 4,6-dichloro-2-hydroxybenzaldehyde, 3,6-diisopropyl-2-hydroxybenzaldehyde, 3,6-ditrimethylsilyl-2-hydroxybenzaldehyde, 3,6-dimethyl-2-hydroxybenzaldehyde, 3,6-diethyl-2-hydroxybenzaldehyde, 3,6-di-n-propyl-2-hydroxybenzaldehyde, 3,6-di-n-butyl-2-hydroxybenzaldehyde, 3,6-diphenyl-2-hydroxybenzaldehyde, 3,6-ditolyl-2-hydroxybenzaldehyde, 3,6-dinaphthyl-2-hydroxybenzaldehyde, 3,6-diadamantyl-2-hydroxybenzaldehyde, 3,6-dinorbornyl-2-hydroxybenzaldehyde, 3,6-difluoro-2-hydroxybenzaldehyde, 3,6-dichloro-2-hydroxybenzaldehyde, 4-isopropyl-2-hydroxybenzaldehyde, 4-trimethylsilyl-2-hydroxybenzaldehyde, 4-methyl-2-hydroxybenzaldehyde, 4-ethyl-2-hydroxybenzaldehyde, 4-n-propyl-2-hydroxybenzaldehyde, 4-n-butyl-2-hydroxybenzaldehyde, 4-phenyl-2-hydroxybenzaldehyde, 4-tolyl-2-hydroxybenzaldehyde, 4-naphthyl-2-hydroxybenzaldehyde, 4-adamantyl-2-hydroxybenzaldehyde, 4-norbornyl-2-hydroxybenzaldehyde, 4-fluoro-2-hydroxybenzaldehyde, 4-chloro-2-hydroxybenzaldehyde, 4-isopropyl-2-hydroxybenzaldehyde, 3-trimethylsilyl-2-hydroxybenzaldehyde, 3-methyl-2-hydroxybenzaldehyde, 3-ethyl-2-hydroxybenzaldehyde, 3-n-propyl-2-hydroxybenzaldehyde, 3-n-butyl-2-hydroxybenzaldehyde, 3-phenyl-2-hydroxybenzaldehyde, 3-tolyl-2-hydroxybenzaldehyde, 3-naphthyl-2-hydroxybenzaldehyde, 3-adamantyl-2-hydroxybenzaldehyde, 3-norbornyl-2-hydroxybenzaldehyde, 3-fluoro-2-hydroxybenzaldehyde, 3-chloro-2-hydroxybenzaldehyde, 5-isopropyl-2-hydroxybenzaldehyde, 5-trimethylsilyl-2-hydroxybenzaldehyde, 5-methyl-2-hydroxybenzaldehyde, 5-ethyl-2-hydroxybenzaldehyde, 5-n-propyl-2-hydroxybenzaldehyde, 5-n-butyl-2-hydroxybenzaldehyde, 5-phenyl-2-hydroxybenzaldehyde, 5-tolyl-2-hydroxybenzaldehyde, 5-naphthyl-2-hydroxybenzaldehyde, 5-adamantyl-2-hydroxybenzaldehyde, 5-norbornyl-2-hydroxybenzaldehyde, 5-fluoro-2-hydroxybenzaldehyde, 5-chloro-2-hydroxybenzaldehyde, 4-isopropyl-2-hydroxybenzaldehyde, 6-trimethylsilyl-2-hydroxybenzaldehyde, 6-methyl-2-hydroxybenzaldehyde, 6-ethyl-2-hydroxybenzaldehyde, 6-n-propyl-2-hydroxybenzaldehyde, 6-n-butyl-2-hydroxybenzaldehyde, 6-phenyl-2-hydroxybenzaldehyde, 6-tolyl-2-hydroxybenzaldehyde, 6-naphthyl-2-hydroxybenzaldehyde, 6-adamantyl-2-hydroxybenzaldehyde, 6-norbornyl-2-hydroxybenzaldehyde, 6-fluoro-2-hydroxybenzaldehyde, 6-chloro-2-hydroxybenzaldehyde, 3,4,5,6-tetrafluoro-2-hydroxybenzaldehyde, 3,4,5,6-tetrachloro-2-hydroxybenzaldehyde, 3,5,6-trifluoro-2-hydroxybenzaldehyde, 3,5,6-trichloro-2-hydroxybenzaldehyde, 1-[3,5-di(tert-butyl)-2-hydroxyphenyl]propan-1-one, 1-[3,5-di(tert-butyl)-2-hydroxyphenyl]pentan-1-one, 1-[3,5-di(tert-butyl)-2-hydroxyphenyl]hexan-1-one, 1-(2-hydroxyphenyl)propan-1-one, 1-(2-hydroxyphenyl)pentan-1-one, 1-(2-hydroxyphenyl)hexan-1-one, 1[3,5-di(tert-butyl)-2-hydroxyphenyl]pyridin-1-one, In the next step, one or more compounds of the formula (V) can be placed in a reaction vessel. The compounds can be suspended in a solvent or else can be present in pure form. Solvents used are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers such as diethyl ether, methyl tert-butyl ether, dimethoxyethane, diisopropyl ether, di-n-butyl ether, anisole, methanol, ethanol, isopropanol and butanol or mixtures of these. The initial charge is placed in the reaction vessel at temperatures of from −100° C. to 300° C., preferably from −80° C. to 200° C., particularly preferably at temperatures of from 20° C. to 150° C.

The addition can subsequently be effected according to route A or B. These routes differ only in the deprotonation reagents used.

In the route A, use is made of organometallic compounds of which nonlimiting examples are: n-butyllithium, sec-butyllithium, tert-butyllithium, methyllithium.

In the route B, use is made of nitrogen-containing bases of which nonlimiting examples are: triethylamine, triisopropylamine, N,N-dimethyisopropylamine, N,N-dimethylethylamine, N,N-dimethylcyclohexylamine, N,N-diethylcyclohexylamine, N,N-dimethylisopropylamine, N,N-diethylbenzylamine, N,N-dimethyl-p-toluidine, N,N-diethyl-p-toluidine, N,N-dimethylbenzylamine, N,N-diethylisopropylamine, N,N-diisopropylmethylamine, N,N-diisopropylethylamine, N,N-dimethylcyclopentylamine, N,N-dimethylcycloheptenylamine, N,N-dimethylcyclooctanylamine, N,N-dimethylnonanoylamine, N,N-diethylcyclopentylamine, N,N-diethylcycloheptenylamine, N,N-diethylcyclooctanylamine, N, N-diethylnonanoylamine.

The reaction of one or more compounds of the formula (V) can be carried out according to route A or B. These compounds of the formula (V) can likewise be suspended in a solvent or be present in pure form. Solvents used are those which have been described above, and preference is given to using the same solvent. The addition can be carried out over a period of from 1 minute to 96 hours. Preference is given to addition over a period of from 10 minutes to 16 hours. The temperature of the initial charge during the addition is from −100° C. to 200° C. Preference is given to temperatures of from −80° C. to 150° C. Particular preference is given to temperatures of from 20° C. to 150° C. The temperature is selected so that at least one reactant is liquid. The subsequent reaction temperature is in a preferred temperature range from 20° C. to 150° C. Furthermore, the reaction can be carried out at atmospheric pressure, but it can also be carried out at superatmospheric pressure, though this requires appropriate reactors. The stoichiometric ratios correspond to those described above. The novel compounds of the formula (I) are formed by this reaction. The reaction sequence to give the compounds of the formula (II) is analogous; instead of the compounds of the formulae (III) and (V), this reaction sequence is carried out using compounds of the formulae (VII) and (VIII),

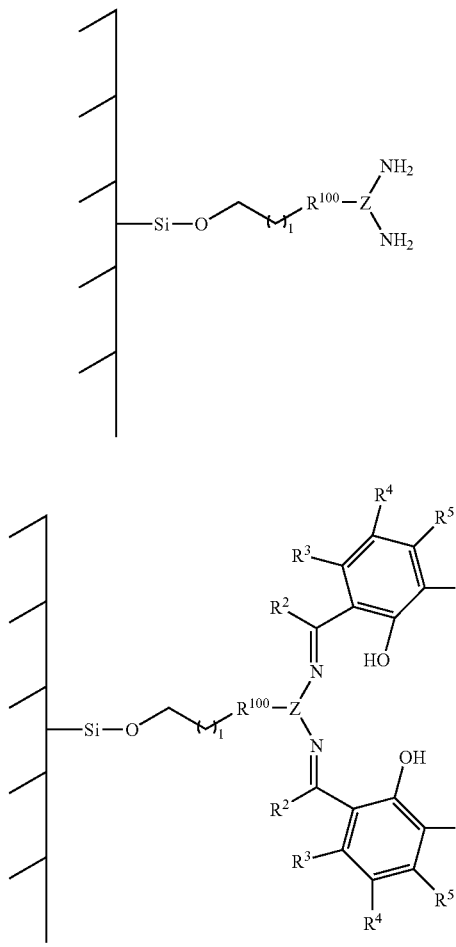

where the radicals are as defined above.

The present invention also provides a catalyst system comprising the novel chemical compound of the formula (I) or compounds of the formula (II).

The novel metal complexes of the formula (I) or formula (II) are particularly useful as constituents of catalyst systems for preparing polyolefins by polymerization of at least one olefin in the presence of a catalyst comprising at least one cocatalyst and at least one metal complex.

The cocatalyst which together with a novel transition metal complex of the formula (I) or (II) forms the catalyst system comprises at least one compound such as an aluminoxane or a Lewis acid or an ionic compound which reacts with an organometallic compound to convert it into a cationic compound.

As aluminoxane, preference is given to using a compound of the general formula (XII)

Further suitable aluminoxanes can, for example, be cyclic as in the formula (XIII)

or linear as in the formula (XIV)

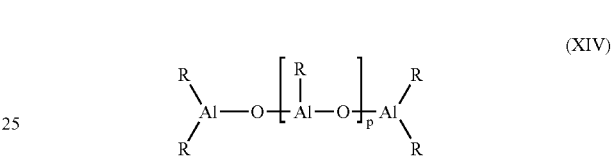

or of the cluster type as in the formula (XV)

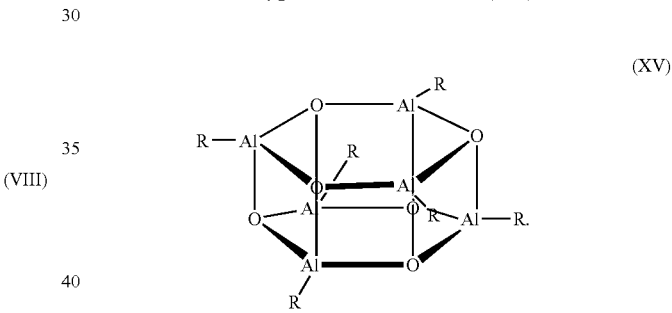

Such aluminoxanes are described, for example, in JACS 117 (1995), 6465–74, Organometallics 13 (1994), 2957–2969.

The radicals R in the formulae (XII), (XIII), (XIV) and (XV) can be identical or different and can each be a $C_1$–$C_{20}$-hydrocarbon group such as a $C_1$–$C_6$-alkyl group, a $C_6$–$C_{18}$-aryl group, benzyl or hydrogen and p is an integer from 2 to 50, preferably from 10 to 35.

The radicals R are preferably identical and are each methyl, isobutyl, n-butyl, phenyl or benzyl, particularly preferably methyl.

If the radicals R are different, they are preferably methyl and hydrogen, methyl and isobutyl or methyl and n-butyl, with hydrogen or isobutyl or n-butyl preferably being present in a proportion of 0.01–40% (number of radicals R).

The aluminoxane can be prepared in various ways by known methods. One of the methods is, for example, to react an aluminium-hydrocarbon compound and/or a hydridoaluminium-hydrocarbon compound with water (gaseous, solid, liquid or bound, for example as water of crystallization) in an inert solvent (e.g. toluene). To prepare an aluminoxane having different alkyl groups R, two different trialkylaluminiums ($AlR_3$+$AlR'_3$) corresponding to the desired composition and reactivity are reacted with water (cf. S. Pasynkiewicz, Polyhedron 9 (1990) 429 and EP-A-0,302,424).

Regardless of the way in which they are prepared, all aluminoxane solutions have a varying content of unreacted aluminium starting compound which is present in free form or as adduct.

As Lewis acid, preference is given to using at least one organoboron or organoaluminium compound containing $C_1$–$C_{20}$ groups such as branched or unbranched alkyl or haloalkyl, e.g. methyl, propyl, isopropyl, isobutyl, trifluoromethyl, unsaturated groups such as aryl or haloaryl, e.g. phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Examples of Lewis acids are trimethylaluminium, triethylaluminium, triisobutylaluminium, tributylaluminium, trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane and/or tris(3,4,5-trifluorophenyl)borane. Particular preference is given to tris(pentafluorophenyl)borane.

As ionic cocatalysts, preference is given to using compounds which contain a noncoordinating anion such as tetrakis(pentafluorophenyl)borate, tetraphenylborate, $SbF_6^-$, $CF_3SO_3^-$ or $ClO_4^-$. Cationic counterions used are protonated Lewis bases such as methylamine, aniline, N,N-dimethylbenzylamine and derivatives, N,N-dimethylcyclohexylamine and derivatives, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or
N,N-dimethylanilinium tetrakis(pentafluorophenyl)borate,
N,N-dimethylbenzylammonium tetrakis(pentafluorophenyl)borate,
N,N-dimethylcyclohexylammonium tetrakis(pentafluorophenyl)borate.

It is also possible to use mixtures of at least one Lewis acid and at least one ionic compound.

Cocatalyst components which are likewise of importance are borane or carborane compounds such as
7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14), bis(tri(butyl)ammonium) nonaborate,
bis(tri(butyl)ammonium) undecaborate,
bis(tri(butyl)ammonium) dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(II).

Further cocatalyst systems which are likewise of importance are combinations of at least one of the abovementioned amines and a support with organoelement compounds as are described in WO 99/40129.

Preferred constituents of these cocatalyst systems are the compounds of the formulae (A) and (B),

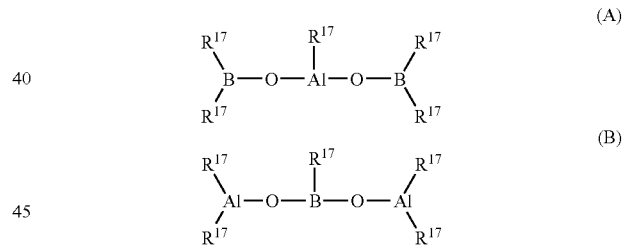

where
$R^{17}$ is a hydrogen atom, a halogen atom, a $C_1$–$C_{40}$ group, in particular $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl. $R^{17}$ can also be an —$OSiR^{18}_3$ group, where the radicals $R^{18}$ are identical or different and are as defined for $R^{17}$.

Further preferred cocatalysts are compounds in general which are formed by reacting at least one compound of the formula (C) and/or (D) and/or (E) with at least one compound of the formula (F),

-continued

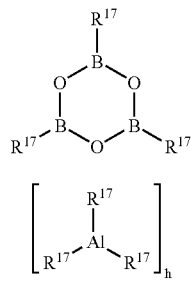
(E)

(F)

where
R[80] can be a hydrogen atom or a boron-free $C_1$–$C_{40}$ group such as $C_1$–$C_{20}$-alkyl, $C_6$–$C_{20}$-aryl, $C_7$–$C_{40}$-arylalkyl, $C_7$–$C_{40}$-alkylaryl, and R[17] is as defined above, X[1] is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl, D is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl, v is an integer from 0 to 3, s is an integer from 0 to 3, h is an integer from 1 to 10, B is boron, Al is aluminium.

If desired, the organoelement compounds are combined with an organometallic compound of the formulae XII to XV and/or XVI [M[40]R[19]$_b$]$_d$, where M[40] is an element of main group I, II or III or the Periodic Table of the Elements, the radicals R[19] are identical or different and are each a hydrogen atom, a halogen atom, a $C_1$–$C_{40}$ group, in particular a $C_1$–$C_{20}$-alkyl, $C_6$–$C_{40}$-aryl, $C_7$–$C_{40}$-arylalkyl or $C_7$–$C_{40}$-alkylaryl group, b is an integer from 1 to 3 and d is an integer from 1 to 4.

Examples of cocatalytically active compounds of the formulae A and B are

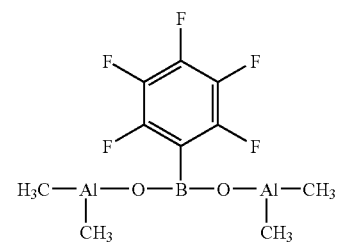

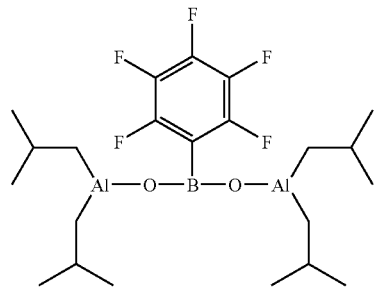

-continued

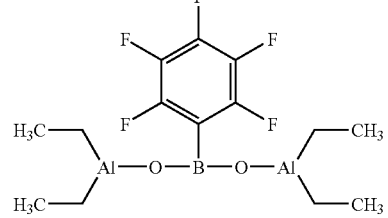

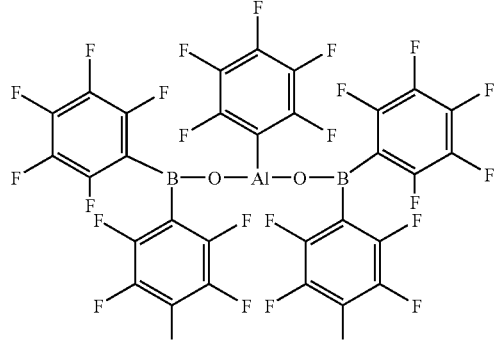

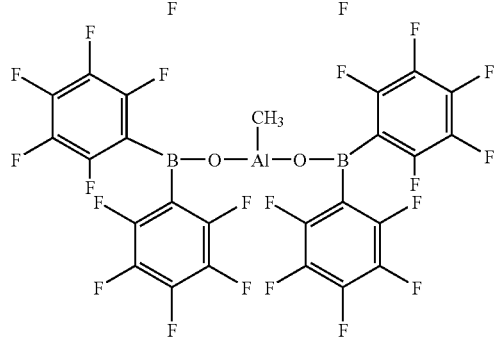

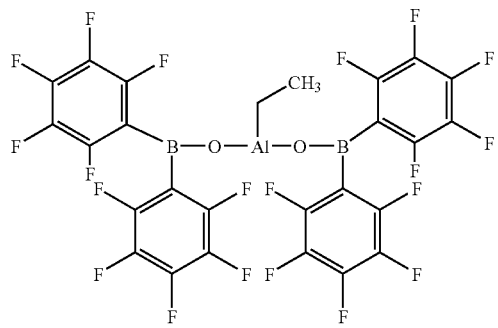

The organometallic compounds of the formula XVI are preferably uncharged Lewis acids in which M[40] is lithium, magnesium and/or aluminium, in particular aluminium. Examples of preferred organometallic compounds of the formula XII are trimethylaluminium, triethylaluminium, triisopropylaluminium, trihexylaluminium, trioctylaluminium, tri-n-butylaluminium, tri-n-propylaluminium, triisoprenylaluminium, dimethylaluminium monochloride, diethylaluminium monochloride, diisobutylaluminium monochloride, methylaluminium sesquichloride, ethylaluminium sesquichloride, dimethylaluminium hydride, diethylaluminium hydride, diisopropylaluminium hydride, dimethylaluminium trimethylsiloxide, dimethylaluminium triethylsiloxide, phenylalane, pentafluorophenylalane and o-tolylalane.

As further cocatalysts, which can be in unsupported or supported form, it is possible to use the compounds described in EP-A-924223, DE-A-19622207, EP-A-601830, EP-A-824112, EP-A-824113, EP-A-811627, WO 97/11775 and DE-A-19606167.

The support component of the amino phase of the catalyst system of the invention can be any organic or inorganic, inert solid, in particular a porous support such as talc, inorganic oxides and finely divided polymer powders (e.g. highly porous polyolefins such as polyethylene and polypropylene and also polystyrenes whose particle size and pore volume are similar to those of silica).

Suitable inorganic oxides may be found in main groups II–VI of the Periodic Table and transition groups III–IV of the Periodic Table of the Elements. Examples of oxides preferred as supports include silicon dioxide, aluminium oxide and also mixed oxides of the elements calcium, aluminium, silicon, magnesium, titanium and corresponding oxide mixtures. Other inorganic oxides which can be used either alone or in combination with the abovementioned preferred oxidic supports are, for example, MgO, $ZrO_2$, $TiO_2$ or $B_2O_3$, to name only a few.

The support materials used have a specific surface area in the range from 10 to 1000 $m^2/g$, a pore volume in the range from 0.1 to 5 ml/g and a mean particle size of from 1 to 500 µm. Preference is given to supports having a specific surface area in the range from 50 to 500 µm, a pore volume in the range from 0.5 to 3.5 ml/g and a mean particle size in the range from 5 to 350 µm. Particular preference is given to supports having a specific surface area in the range from 200 to 400 $m^2/g$, a pore volume in the range from 0.8 to 3.0 ml/g and a mean particle size of from 10 to 200 µm.

If the support material used naturally has a low moisture content or residual solvent content, dehydration or drying before use can be omitted. If this is not the case, as when silica gel is used as support material, dehydration or drying is advisable. Thermal dehydration or drying of the support material can be carried out under reduced pressure with simultaneous blanketing with inert gas (e.g. nitrogen). The drying temperature is in the range from 100 to 1000° C., preferably from 200 to 800° C. The parameter of pressure is not critical in this case. The duration of the drying process can be from 1 to 24 hours. Shorter or longer drying times are possible, provided that equilibrium with the hydroxyl groups on the support surface can be established under the chosen conditions, which normally takes from 4 to 8 hours. Dehydration or drying of the support material can also be carried out by chemical means, by reacting the adsorbed water and the hydroxyl groups on the surface with suitable passivating agents. Reaction with the passivating reagent enables the hydroxyl groups to be converted completely or partly into a form which does not lead to any adverse interaction with the catalytically active sites. Suitable passivating agents are, for example, silicon halides and silanes, e.g. silicon tetrachloride, chlorotrimethylsilane, dimethylaminotrichlorosilane, or organometallic compounds of aluminium, boron and magnesium, for example trimethylaluminium, triethylaluminium, triisobutylaluminium, triethylborane, dibutylmagnesium. The chemical dehydration or passivation of the support material is carried out, for example, by reacting a suspension of the support material in a suitable solvent with the passivating reagent in pure form or as a solution in a suitable solvent in the absence of air and moisture. Suitable solvents are, for example, aliphatic or aromatic hydrocarbons such as pentane, hexane, heptane, toluene or xylene. Passivation is carried out at temperatures in the range from 25° C. to 120° C., preferably from 50 to 70° C. Higher and lower temperatures are possible. The reaction time is from 30 minutes to 20 hours, preferably from 1 to 5 hours. After chemical dehydration has proceeded to completion, the support material is isolated by filtration under inert conditions, washed one or more times with suitable inert solvents as have been described above, and subsequently dried in a stream of inert gas or under reduced pressure.

To prepare the supported catalyst system, at least one of the above-described covalently fixed transition metal compounds of the formula (I) or (II) in a suitable solvent is brought into contact with at least one cocatalyst component, preferably giving an adduct or a mixture The solvent is subsequently removed and the resulting supported transition metal catalyst system is dried to ensure that all or most of the solvent is removed from the pores of the support material. The supported catalyst is obtained as a free-flowing powder.

A process for preparing a free-flowing and, if desired, prepolymerized transition metal catalyst system comprises the following steps:
 a) preparation of a covalently fixed transition metal compound/cocatalyst mixture in a suitable solvent or suspension medium, with the covalently fixed transition metal component having one of the above-described structures,
 b) removal of the major part of the solvent from the resulting mixture,
 c) isolation of the supported catalyst system,
 d) if desired, prepolymerization of the resulting supported catalyst system with one or more olefinic monomer(s) to give a prepolymerized supported catalyst system.

Preferred solvents for the preparation of the covalently fixed transition metal compound/cocatalyst mixture are hydrocarbons and hydrocarbon mixtures which are liquid at the chosen reaction temperature and in which at least one of the individual components preferably dissolves. However, solubility of the individual components is not a prerequisite as long as it is ensured that the reaction product of transition metal compound and cocatalyst components is soluble in the solvent selected. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and transition metal compound used in the preparation of the supported catalyst system can be varied over a wide range. Preference is given to a molar ratio of aluminium to transition metal in the transition metal compounds of from 10:1 to 1000:1, very particularly preferably from 50:1 to 500:1. In the case of methylaluminoxane, preference is given to using 30% strength solutions in toluene, but the use of 10% strength solutions is also possible. Preactivation is carried out by suspending the covalently fixed transition metal compound in the form of a solid in a solution of the aluminoxane in a suitable solvent. It is also possible to suspend the covalently fixed transition metal compound separately in a suitable solvent and subsequently to combine this solution with the aluminoxane solution. Preference is given to using toluene.

The preactivation time is from 1 minute to 200 hours.

The preactivation can take place at room temperature (25° C.). The use of higher temperatures can in individual cases shorten the preactivation time required and effect an additional increase in activity. In this case, "higher temperatures" means a range from 50 to 100° C.

The volume of the preactivated solution or of the covalently fixed transition metal compound/cocatalyst mixture can exceed 100% of the total pore volume of the support material used or else can be up to 100% of the total pore volume.

All or most of the solvent is subsequently removed from the supported catalyst system, with the mixture being able to be stirred and, if appropriate, also heated. Preference is given to removing both the visible proportion of the solvent and also the proportion present in the pores of the support material. Removal of the solvent can be carried out in a conventional way under reduced pressure and/or with flushing with inert gas. In the drying procedure, the mixture can be heated until the free solvent has been removed, which usually takes from 1 to 3 hours at a preferred temperature in the range from 30 to 60° C. The free solvent is the visible proportion of solvent in the mixture. For the purposes of the present invention, residual solvent is the proportion which is enclosed in the pores. As an alternative to complete removal of the solvent, the supported catalyst system can also be dried only to a particular residual solvent content, with the free solvent having been completely removed. The supported catalyst system can subsequently be washed with a low-boiling hydrocarbon such as pentane or hexane and dried again.

The supported catalyst system prepared according to the invention can either be used directly for the polymerization of olefins or can be prepolymerized with one or more olefinic monomers before being used in a polymerization process. The procedure for prepolymerization of supported catalyst systems is described, for example, in WO 94/28034.

A small amount of an olefin, preferably an α-olefin (for example vinylcyclohexane, styrene or phenyldimethylvinylsilane), as modifying component or an antistatic (as described in U.S. Ser. No. 08/365280) can be added as additive during or after the preparation of the supported catalyst system. The molar ratio of additive to organometallic compound I is preferably from 1:1000 to 1000:1, very particularly preferably from 1:20 to 20:1.

The present invention also provides a process for preparing a polyolefin by polymerization of one or more olefins in the presence of the catalyst system of the invention comprising at least one transition metal component of the formula VII. For the purposes of the present invention, the term polymerization encompasses both homopolymerization and copolymerization.

Preference is given to polymerizing olefins of the formula $R_m$—CH=CH—$R_n$, where $R_m$ and $R_n$ are identical or different and are each a hydrogen atom or a carbon-containing radical having from 1 to 20 carbon atoms, in particular from 1 to 10 carbon atoms, and $R_m$ and $R_n$ together with the atoms connecting them can form one or more rings.

Examples of such olefins or functionalized olefins are 1-olefins having 2–20, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene, vinyl acetate, methyl methacrylate. In the process of the invention, preference is given to homopolymerizing ethene or propene, or copolymerizing propene with ethene and/or with one or more 1-olefins or functionalized olefins having from 4 to 20 carbon atoms, e.g. butene, hexene, styrene or vinylcyclohexane, vinyl acetate, methyl methacrylate, and/or one or more dienes having from 4 to 20 carbon atoms, e.g. 1,4-butadiene, norbornadiene, ethylidenenorbornene or ethyinorbornadiene. Examples of such copolymers are ethene/propene copolymers, ethene/norbornene copolymers, ethene/styrene copolymers and ethene/propene/1,4-hexadiene terpolymers. The polymerization is carried out at a temperature of from 0 to 300° C., preferably from 50 to 200° C., very particularly preferably 50–80° C. The pressure is from 0.5 to 2000 bar, preferably from 5 to 64 bar.

The polymerization can be carried out in solution, in bulk, in suspension or in the gas phase, continuously or batchwise, in one or more stages.

The catalyst system prepared according to the invention can be used as sole catalyst component for the polymerization of olefins having from 2 to 20 carbon atoms, or can be preferably used in combination with at least one alkyl compound of the elements of main groups I to III of the Periodic Table, e.g. an aluminium alkyl, magnesium alkyl or lithium alkyl or an aluminoxane. The alkyl compound is added to the monomer or suspension medium and serves to free the monomer of substances which could adversely affect the catalyst activity. The amount of alkyl compound added depends on the quality of the monomers used.

Hydrogen is added, if necessary, as molar mass regulator and/or to increase the activity.

The catalyst system can be introduced into the polymerization system in pure form or can be admixed with inert components such as paraffins, oils or waxes to improve meterability. In addition, an antistatic can be introduced into the polymerization system either together with or separately from the catalyst system used.

The polymers prepared using the catalyst system of the invention display a uniform particle morphology and contain no fines. In the polymerization using the catalyst system of the invention, no deposits or caked material are formed.

The copolymers obtained using the catalyst system of the invention can be prepared with high productivity at industrially relevant process parameters without deposit formation. They thus make it possible to prepare copolymers having high comonomer incorporation and a high molar mass.

The invention is illustrated by the following nonlimiting examples.

General information: preparation and handling of the organometallic compounds were carried out in the absence of air and moisture under argon (Schlenk technique or glove box). All solvents required were purged with argon and dried over molecular sieves before use.

The preparation of the imine starting materials proceeds according to the processes described in the literature. Examples may be found, for example, in Chem. Rev. 1963, 63, 489–510. Some of them are commercially available chemicals.

Preparation of the Covalently Supported Imines:

1. Reaction of Lichroprep $NH_2$ with Salicylaldehyde 0.192 g (1.57 mmol) of salicylaldehyde together with 30 ml of methanol are placed in a reaction vessel and 20 μl of glacial acetic acid are added. 2.01 g of the polymer support Lichroprep $NH_2$ (from Merck) are subsequently added as a solid at room temperature. The reaction suspension is subsequently refluxed for 7 hours and then stirred overnight at room temperature. The suspension is subsequently filtered through a G3 frit, and the now yellow solid is washed twice with 5 ml each time of methanol. The yellow solid is dried to constant weight in an oil pump vacuum. 2.14 g were isolated.

2. Reaction of the Modified Support to Form the Covalently Supported Metal Complex 2 g of the support prepared above are suspended in 100 ml of THF and cooled down to −78° C. 0.242 ml of a 2.5M butyllithium solution is subsequently added dropwise. After the addition is complete, the suspension is allowed to warm to room temperature and is stirred for 2 hours at this temperature. The reaction mixture is subsequently cooled down to 0° C. and a solution of 0.083 g (0.26 mmol) of $ZrCl_4$*DME in 100 ml of THF is added dropwise. The mixture is allowed to warm to room temperature and is stirred overnight. The precipitate is isolated by means of a G3 frit and washed twice with 25 ml each time of THF. The yellow solid is then dried to constant weight in an oil pump vacuum. 2.08 g of the covalently supported complex are isolated.

The invention claimed is:

1. Compounds of the formula (I)

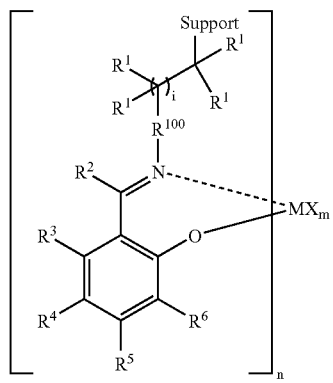

where

M is a metal of transition group III, IV, V or VI of the Periodic Table of the Elements, $R^1$, $R^2$, $R^3$, $R^4$, $R^5$, $R^6$ are identical or different and are each a hydrogen atom, a halogen atom or $Si(R^{10})_3$, where the radicals $R^{10}$ are identical or different and are each a hydrogen atom or a $C_1$–$C_{40}$ group, or $R^1$, $R^2$, $R^3$, $R^4$, $R^5$, $R^6$ are identical or different and are each a $C_1$–$C_{30}$ group, or two or more radicals $R^1$ and/or two or more radicals $R^2$ to $R^6$ can be joined to one another in such a way that the radicals $R^1$ or $R^2$ to $R^6$ and $R^{10}$ and the atoms connecting them form a $C_4$–$C_{24}$ ring system which may in turn be substituted, and the radicals $R^{100}$ are identical or different and can each be a $C_1$–$C_{40}$ group, and n is an integer from 1 to 4, and m is an integer from 0 to 4, and i is an integer from 1 to 100, and the radicals X can be identical or different and are each a hydrogen atom, a $C_1$–$C_{10}$-hydrocarbon group, or $OR^9$, $SR^9$, $OSiR_3^9$, $SiR_3^9$, $PR_2^9$ or $NR_2^9$, where $R^9$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or the radicals L are each a toluenesulphonyl, trifluoroacetyl, trifluoracetoxyl, trifluoromethanesulphonyl, nonafluorobutanesulphonyl or 2,2,2-trifluoromethanesulphonyl group.

2. Compounds according to claim 1, characterized in that M is Ti, Zr or Hf and $R^1$, $R^2$, $R^3$, $R^4$, $R^5$, $R^6$ are identical or different and are each a hydrogen atom, a halogen atom or $Si(R^{10})_3$, where the radicals $R^{10}$ are identical or different and are each a hydrogen atom or a $C_1$–$C_{40}$ group as defined above or $R^1$, $R^2$, $R^3$, $R^4$, $R^5$, $R^6$ are identical or different and are each a $C_1$–$C_{30}$ group as defined above, or two or more radicals $R^1$ and/or two or more radicals $R^2$ to $R^6$ can be joined to one another in such a way that the radicals $R^1$ or $R^2$ to $R^6$ and $R^{10}$ and the atoms connecting them form a $C_4$–$C_{24}$ ring system which may in turn be substituted, and the radicals $R^{100}$ are identical or different and are each a $C_1$–$C_{40}$ group, and n is an integer from 1 to 4, and m is an integer from 0 to 4, and i is an integer from 1 to 100, and X is a halogen atom, a $C_1$–$C_{18}$ alkyl group, a $C_6$–$C_{15}$-aryl group, or substituted or unsubstituted phenoxides.

3. Compounds according to claim 1, characterized in that M is zirconium, $R^1$, $R^2$, $R^3$, $R^4$, $R^5$, $R^6$ are each a hydrogen atom or a linear or branched $C_1$–$C_{12}$-alkyl group, or a halogen atom or $C_5$–$C_{18}$-heteroaryl, or $C_7$–$C_{12}$-arylalkyl, or $C_7$–$C_{12}$-alkylaryl, or fluorinated $C_1$–$C_8$-alkyl, or fluorinated $C_6$–$C_{18}$-aryl, or fluorinated $C_7$–$C_{12}$-arylalkyl or fluorinated $C_7$–$C_{12}$-alkylaryl, and the radicals $R^{100}$ are identical or different and are each $C_1$–$C_{20}$-alkyl, methylene, ethylene, $C_1$–$C_{10}$-fluoroalkyl, -$C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, fluorinated $C_1$–$C_{25}$-alkyl, and n is 2, and m is 2, and i is 3, 4, 5, 6, 7, 8, 9 or 10, and X is a halogen atom, a $C_1$–$C_{18}$-alkyl group, a $C_6$–$C_{15}$-aryl group, or substituted or unsubstituted phenoxides.

4. Catalyst system comprising at least one compound according to claim 1 and at least one cocatalyst.

5. Catalyst system according to claim 4, wherein said cocatalyst is an aluminoxane or a Lewis acid or an ionic compound.

6. Compounds according to claim 1, wherein X are identical or different and are each a hydrogen atom, $C_1$–$C_{10}$-alkyl or $C_6$–$C_{10}$-aryl, a halogen atom or $OR^9$, $SR^9$, $OSiR_3^9$, $SiR_3^9$, $PR_2^9$ or $NR_2^9$.

7. Compounds according to claim 2, wherein X are independently a chlorine atom, methyl, ethyl, n-propyl, i-propyl, tert-butyl, n-pentyl, n-hexyl, cyclohexyl, octyl, a $C_6$–$C_{15}$-aryl group, or substituted or unsubstituted phenoxides.

8. Compounds according to claim 2, wherein

M is zirconium, $R^1$, $R^2$, $R^3$, $R^4$, $R^5$, $R^6$ independently are each a hydrogen atom, methyl, ethyl, n-butyl, n-hexyl, isopropyl, isobutyl, isopentyl, cyclohexyl, cyclopentyl or octyl, a halogen atom, $C_5$–$C_{18}$-heteroaryl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, and the radicals $R^{100}$ are identical or different and are each $C_1$–$C_{20}$-alkyl, methylene, ethylene, $C_1$–$C_{10}$-fluoroalkyl, $C_1$–$C_{10}$-alkoxy, phenyl, biphenyl, 1,2,4,5-tetrafluorophenyl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, fluorinated $C_1$–$C_{25}$-alkyl, and n is 2, and m is 2, and i is 3, 4, 5, 6, 7, 8, 9 or 10, and X is a chlorine atom, methyl, ethyl, n-butyl, n-hexyl, isopropyl, isobutyl, isopentyl, cyclohexyl, cyclopentyl, octyl, $C_6$–$C_{15}$-aryl group, or substituted or unsubstituted phenoxides.

9. Compounds according to claim 8, wherein $R^1$, $R^2$, $R^3$, $R^4$, $R^5$, $R^6$ independently are each a hydrogen atom, methyl, ethyl, isopropyl or cyclohexyl, and the radicals $R^{100}$ are identical or different and are each methylene.

10. A process of polymerization of olefins which comprises polymerizing an olefin with the catalyst system according to claim 4.

11. The process according to claim 10, wherein the olefin has the formula $R_m$—CH=CH—$R_n$, where $R_m$ and $R_n$ are identical or different and are each a hydrogen atom or a carbon-containing radical having from 1 to 20 carbon atoms, or $R_m$ and $R_n$ together with the atoms connecting them can form one or more rings.

12. The process according to claim 11, wherein $R_m$ and $R_n$ are identical or different and are each a hydrogen atom or a carbon-containing radical having from 1 to 10 carbon atoms.

13. Compounds of the formula (II)

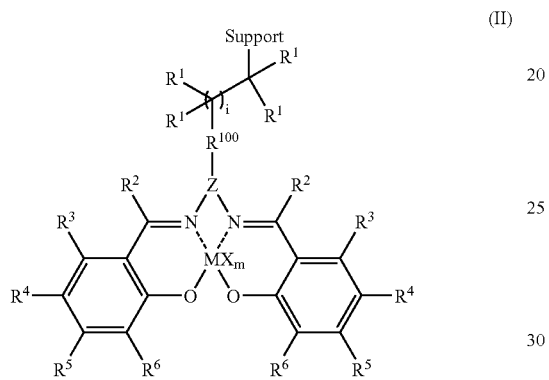

where

M is a metal of transition group III, IV, V or VI of the Periodic Table of the Elements, $R^1$, $R^2$, $R^3$, $R^4$, $R^5$, $R^6$ are identical or different and are each a hydrogen atom, a halogen atom or $Si(R^{10})_3$, where the radicals $R^{10}$ are identical or different and are each a hydrogen atom or a $C_1$–$C_{40}$ group, or $R^1$, $R^2$, $R^3$, $R^4$, $R^5$, $R^6$ are identical or different and are each a $C_1$–$C_{30}$ group, or two or more radicals $R^1$ and/or two or more radicals $R^2$ to $R^6$ can be joined to one another in such a way that the radicals $R^1$ or $R^2$ to $R^6$ and $R^{10}$ and the atoms connecting them form a $C_4$–$C_{24}$ ring system which may in turn be substituted, and the radicals $R^{100}$ are identical or different and can each be a $C_1$–$C_{40}$ group, and m is an integer from 0 to 4, and i is an integer from 1 to 100, and the radicals X can be identical or different and are each a hydrogen atom, a $C_1$–$C_{40}$-hydrocarbon group, a halogen atom or $OR^9$, $SR^9$, $OSiR_3^9$, $SiR_3^9$, $PR_2^9$ or $NR_2^9$, where $R^9$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or the radicals L are each a toluenesulphonyl, trifluoroacetyl, trifluoracetoxyl, trifluoromethanesulphonyl, nonafluorobutanesulphonyl or 2,2,2-trifluoromethanesulphonyl group, and Z is a bridging structural element of the formula $M^5R^{13}R^{14}$, where $M^5$ is silicon or carbon and $R^{13}$ and $R^{14}$ are identical or different and are each a $C_1$–$C_{40}$ group or trimethylsilyl, or Z is boron, sulphur, phosphorus or nitrogen, and the support is a support for the amino functions and is an inorganic polymer, organic polymer or organic copolymer.

14. Compounds according to claim 13, characterized in that silica, polystyrene, polystyrene-divinylbenzene copolymer and polyethylene glycol materials are used as supports.

15. Compounds according to claim 14, characterized in that the support bears an amino group and is attached to the polymer via various spacers.

16. Compounds according to claim 15, characterized in that the support is

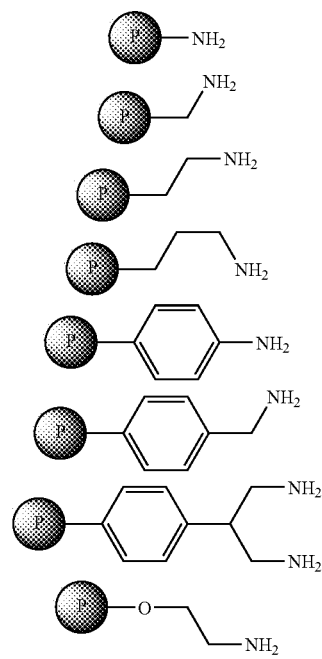

P = Polymer where the polymer is a silica, polystyrene, polystyrene-divinylbenzene copolymer and/or polyethylene glycol material.

17. Compounds according to claim 13, wherein the radicals X can be identical or different and are each a hydrogen atom, a $C_1$–$C_{10}$-alkyl or $C_6$–$C_{10}$-aryl, a halogen atom, $OR^9$, $SR^9$, $OSiR_3^9$, $SiR_3^9$, $PR_2^9$ or $NR_2^9$.

18. Catalyst system comprising at least one compound according to claim 13 and at least one cocatalyst.

19. The catalyst system according to claim 18, wherein said cocatalyst is an aluminoxane, a Lewis acid or an ionic compound.

20. A process of polymerization of olefins which comprises polymerizing an olefin with the catalyst system according to claim 18.

* * * * *

UNITED STATES PATENT AND TRADEMARK OFFICE
CERTIFICATE OF CORRECTION

| | | |
|---|---|---|
| PATENT NO. | : 7,157,398 B2 | Page 1 of 1 |
| APPLICATION NO. | : 10/505684 | |
| DATED | : January 2, 2007 | |
| INVENTOR(S) | : Jörg Schottek et al. | |

It is certified that error appears in the above-identified patent and that said Letters Patent is hereby corrected as shown below:

In the Claims:

In Claim 13, at column 89, line 53, "hydrogen atom, a $C_1$-$C_{40}$-hydrocarbon group, a halo-" should read -- hydrogen atom, a $C_1$-$C_{10}$-hydrocarbon group, a halo- --.

Signed and Sealed this

Third Day of April, 2007

JON W. DUDAS
*Director of the United States Patent and Trademark Office*